United States Patent
Lukatela

(10) Patent No.: US 9,150,278 B2
(45) Date of Patent: Oct. 6, 2015

(54) PEDAL TORQUE MEASUREMENT

(75) Inventor: Zvonimir Thomas Lukatela, Nickol (AU)

(73) Assignee: POWER PEDALS PTY LTD (AU)

( * ) Notice: Subject to any disclaimer, the term of this patent is extended or adjusted under 35 U.S.C. 154(b) by 823 days.

(21) Appl. No.: 13/378,990

(22) PCT Filed: Jun. 17, 2010

(86) PCT No.: PCT/AU2010/000751
§ 371 (c)(1),
(2), (4) Date: Mar. 5, 2012

(87) PCT Pub. No.: WO2010/144964
PCT Pub. Date: Dec. 23, 2010

(65) Prior Publication Data
US 2012/0173167 A1    Jul. 5, 2012

(30) Foreign Application Priority Data

Jun. 18, 2009  (AU) ................................. 2009902814

(51) Int. Cl.
*G06F 19/00*    (2011.01)
*B62M 3/16*    (2006.01)
(Continued)

(52) U.S. Cl.
CPC .................. *B62M 3/16* (2013.01); *G01L 3/108* (2013.01); *G01L 5/225* (2013.01); *A61B 5/221* (2013.01)

(58) Field of Classification Search
CPC ........... B62M 3/00; B62M 3/16; G01L 5/225; A61B 5/221

USPC .............................. 702/42, 44, 182–185, 188
See application file for complete search history.

(56) References Cited

U.S. PATENT DOCUMENTS 4,141,248 A    2/1979  Bargenda
4,463,433 A    7/1984  Hull et al.
(Continued)

FOREIGN PATENT DOCUMENTS

DE    202009001463 U1    6/2009
EP          1980832 A2    10/2008
(Continued)

OTHER PUBLICATIONS

Dorel, S. et al.; "New Instrumented Pedals to Quantify 2D Forces at the Shoe-Pedal Interface in Ecological Conditions: Preliminary Study in Elite Track Cyclists"; *Computer Methods in Biomechanics and Biomechanical Engineering*; 2008; pp. 89-90; Supplemental 1.
(Continued)

*Primary Examiner* — Edward Raymond
(74) *Attorney, Agent, or Firm* — Kilpatrick Townsend & Stockton LLP

(57) ABSTRACT

There is described a method for determining the torque applied to a pedal axle (210) under load. The method comprises measuring the strain experienced by the pedal axle (210) as a result of the load, determining the orientation of the load from the strain measurement, determining the magnitude of the load from the strain measurement and determining torque from the orientation and the magnitude. There is also described a method for determining the orientation of a pedal axle (210) under load. The method comprises measuring the strain experienced by the pedal axle (210) as a result of the load and determining the orientation of the load from the strain measurement.

33 Claims, 12 Drawing Sheets

(51) Int. Cl.
*G01L 5/22* (2006.01)
*G01L 3/10* (2006.01)
*A61B 5/22* (2006.01)

(56) References Cited

U.S. PATENT DOCUMENTS

| | | | |
|---|---|---|---|
| 5,027,303 A | 6/1991 | Witte | |
| 6,263,992 B1 * | 7/2001 | Li | 180/206.3 |
| 7,418,862 B2 | 9/2008 | Gruben et al. | |
| 2007/0137207 A1 | 6/2007 | Mancini et al. | |
| 2008/0236293 A1 | 10/2008 | Meggiolan | |

FOREIGN PATENT DOCUMENTS

| | | |
|---|---|---|
| FR | 2724728 A1 | 3/1996 |
| WO | 2008/109914 A2 | 9/2008 |

OTHER PUBLICATIONS

Gurgel, Jonas et al.; "Development and Calibration of a Pedal with Force and Moment Sensors"; *Proceedings of the 28th IEEE EMBS Annual International Conference;* Aug. 30-Sep. 3, 2006; pp. 4144-4146; vol. FrEP13.11.

Hull, M.L. et al.; "Measurement of Pedal Loading in Bicycling: I. Instrumentation"; *Journal of Biomechanics;* 1981; pp. 843-855; vol. 14; No. 12.

Newmiller, J. et al.; "A Mechanically Decoupled Two Force Component Bicycle Pedal Dynamometer"; *Journal of Biomechanics;* 1988; pp. 375-386; vol. 21; No. 5.

Reiser II, R.F. et al.; "Instrumented Bicycle Pedals for Dynamic Measurement of Propulsive Cycling Loads"; *Sports Engineering;* 2003; pp. 41-48; vol. 6.

Tielert, Reinhardt et al.; "Power Measurement in Cycling Using Inductive Coupling of Energy and Data (P80)"; *The Engineering of Sport 7;* 2008; pp. 397-403; Vo. 1.

International Search Report mailed Aug. 2, 2010, from PCT Application No. PCT/AU2010/000751 (6 pages).

International Preliminary Report on Patentability mailed Sep. 26, 2011, from PCT Application No. PCT/AU2010/000751 (16 pages).

Extended European Search Report mailed Jun. 23, 2014, from European Application No. 10788509.7 (8 pages).

Sanderson David J., "The Influence of Cadence and Power Output on the Biomechanics of Force Application During Steady-Rate Cycling in Competitive and Recreational Cyclists," *Journal of Sport Sciences,* 1991, vol. 9 No. 2, pp. 191-203.

* cited by examiner

PEDAL TORQUE MEASUREMENT

CROSS-REFERENCES TO RELATED APPLICATIONS

This application is a National Stage of International Application No. PCT/AU2010/000751 filed Jun. 17, 2010, and which claims the benefit of Australian Patent Application No. 2009902814, filed Jun. 18, 2009, the disclosures of which are incorporated herein by reference.

TECHNICAL FIELD

This invention relates generally to apparatus such as dynamometers for measuring torque, and more particularly as applied to a bicycle pedal.

BACKGROUND

Existing embodiments of bicycle pedal dynamometers incorporate strain gauges in either the pedal body or pedal axle, such as described in U.S. Pat. No. 4,463,433 (Hull et al).

In order to determine the torque or power applied to a pedal, it is necessary to determine the angular orientation of the applied force. However, in order to establish the angular orientation of the applied force, existing arrangements suffer from the disadvantage of requiring angular position transducers, such as a rotary potentiometer or an electromagnetic/optical encoding transducer. Such arrangements are therefore necessarily bulky, complex and subject to mechanical failure.

SUMMARY

According to one aspect there is provided a method for determining the torque applied to a pedal axle under load. The method comprises measuring the strain experienced by the pedal axle as a result of the load, determining the orientation of the load from the strain measurement, determining the magnitude of the load from the strain measurement and determining torque from the orientation and the magnitude.

According to another aspect there is provided a method for determining the orientation of a pedal axle under load. The method comprises measuring the strain experienced by the pedal axle as a result of the load and determining the orientation of the load from the strain measurement.

According to another aspect there is provided an apparatus for determining the torque applied to a pedal axle under load. The apparatus comprises a strain gauge configured to measure the strain experienced by the pedal axle as a result of the load; and a processor configured to determine the orientation of the load from the strain measurement, to determine the magnitude of the load from the strain measurement and to determine the torque from the orientation and the magnitude.

According to another aspect there is provided an apparatus for determining the orientation of a pedal axle under load. The apparatus comprises a strain gauge configured to measure the strain experienced by the pedal axle as a result of the load and a processor configured determining the orientation of the load from the strain measurement, to determine the magnitude of the load from the strain measurement, and to determine the torque from the orientation and the magnitude.

According to another aspect there is provided a computer readable storage medium having a computer program recorded therein. The program is executable by a computer apparatus to make the computer determine the torque applied to a pedal axle under load. The program comprises code for measuring the strain experienced by the pedal axle as a result of the load, code for determining the orientation of the load from the strain measurement, code for determining the magnitude of the load from the strain measurement and code for determining the torque from the orientation and the magnitude.

According to another aspect there is provided a computer readable storage medium having a computer program recorded therein. The program is executable by a computer apparatus to make the computer determine the orientation of a pedal axle under load. The program comprises code for measuring the strain experienced by the pedal axle as a result of the load and code for determining the orientation of the load from the strain measurement.

BRIEF DESCRIPTION OF THE DRAWINGS

At least one embodiment of the invention will now be described with reference to the drawings, in which.

DETAILED DESCRIPTION

Figure 1A:
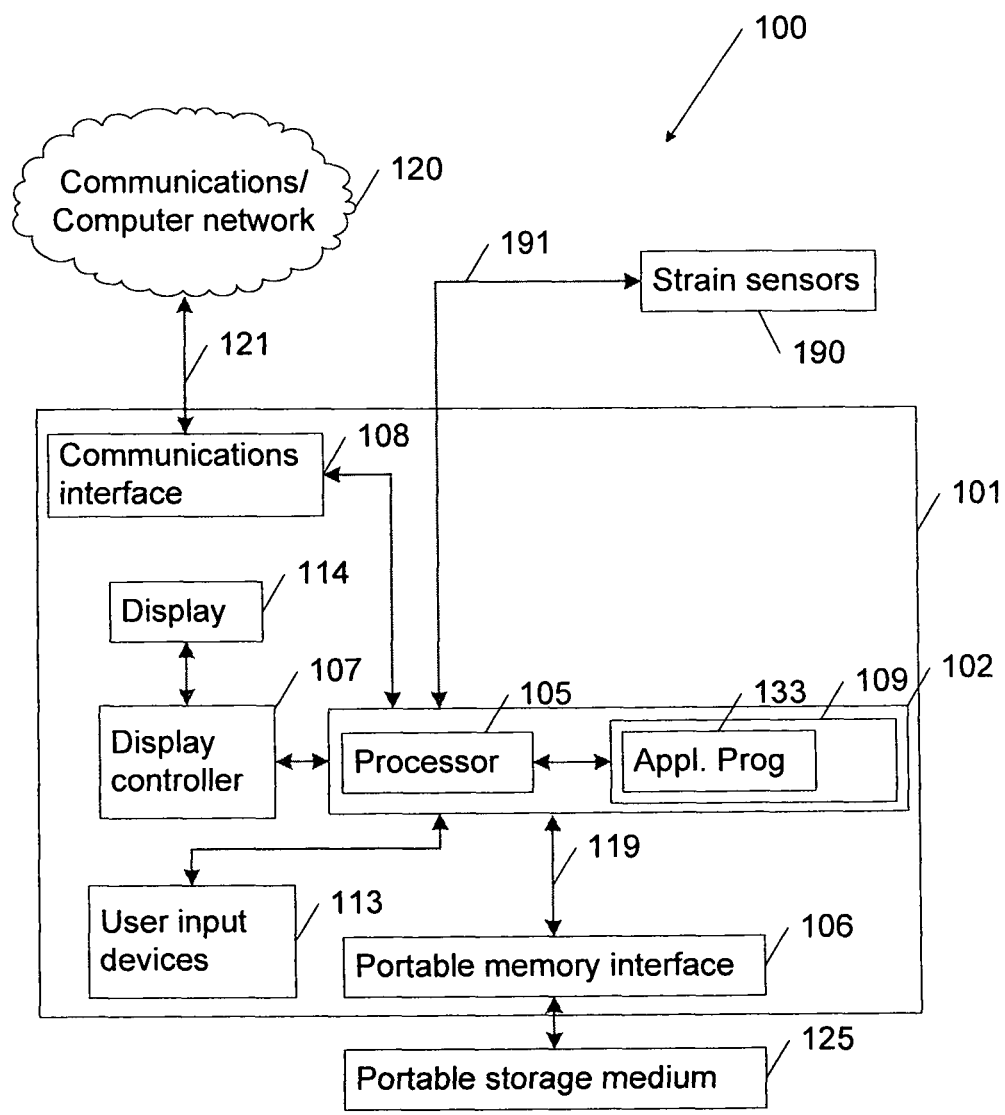
FIGS. 1A and 1B collectively form a schematic block diagram of a general purpose electronic device comprising embedded components.

Where reference is made in any one or more of the accompanying drawings to steps and/or features, which have the same reference numerals, those steps and/or features have for the purposes of this description the same function(s) or operation(s), unless the contrary intention appears.

Hardware

Figure 1B:
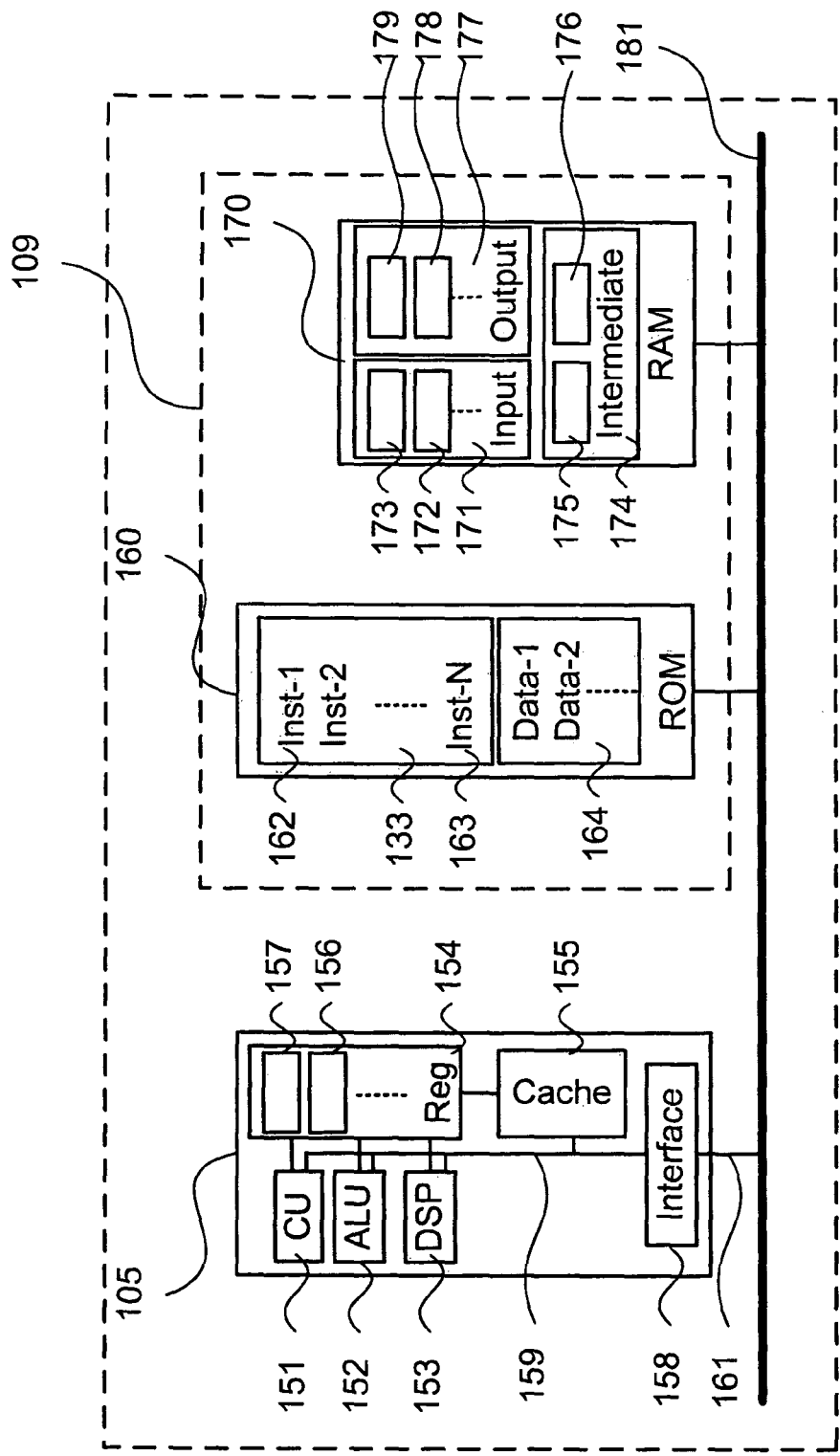

FIGS. 1A and 1B collectively form a schematic block diagram of a general purpose electronic device 101 comprising embedded components, upon which the methods to be described below are desirably practiced. The electronic device 101 is typically a cycle computer, for calculating, displaying, and storing cycle data, such as the torque and power output of a cyclist. Alternatively, the electronic device 101 may also be a higher-level device such as a desktop computer, server computer, or other such devices with significantly larger data processing resources.

As seen in FIG. 1A, the electronic device 101 comprises an embedded controller 102. Accordingly, the electronic device 101 may be referred to as an "embedded device." In the present example, the controller 102 comprises a processing unit (or processor) 105 which is bi-directionally coupled to an internal storage module 109. The storage module 109 may be formed from non-volatile semiconductor read only memory (ROM) 160 and semiconductor random access memory (RAM) 170, as seen in FIG. 1B. The RAM 170 may be volatile, non-volatile or a combination of volatile and non-volatile memory.

The electronic device 101 comprises a display controller 107, which is connected to a video display 114, such as a liquid crystal display (LCD) panel or the like. The display controller 107 is configured for displaying graphical images on the video display 114 in accordance with instructions received from the processor 105.

The electronic device 101 also comprises user input devices 113 which are typically formed by keys, a keypad or like controls. In some implementations, the user input devices 113 may include a touch sensitive panel physically associated with the display 114 to collectively form a touch-screen. Such a touch-screen may thus operate as one form of graphical user interface (GUI) as opposed to a prompt or menu driven GUI typically used with keypad-display combinations.

As seen in FIG. 1A, the electronic device 101 also comprises a portable memory interface 106, which is coupled to the processor 105 via a connection 119. The portable memory interface 106 allows a complementary portable memory device 125 to be coupled to the electronic device 101 to act as a source or destination of data or to supplement the internal storage module 109. Examples of such interfaces permit coupling with portable memory devices such as Universal Serial Bus (USB) memory devices, Secure Digital (SD) cards, Personal Computer Memory Card International Association (PCMIA) cards, optical disks and magnetic disks.

The electronic device 101 also comprises a communications interface 108 to permit coupling of the device 101 to a computer or communications network 120 via a connection 121. The connection 121 may be wired or wireless. For example, the connection 121 may be radio frequency or optical. An example of a wired connection includes Ethernet. Further, an example of wireless connection includes Bluetooth-type local interconnection, Wi-Fi (including protocols based on the standards of the IEEE 802.11 family), Infrared Data Association (IrDa) and the like. As such, using communications interface 108, the electronic device 101 may transmit cycle data in real time to interested parties.

The electronic device 101 is coupled to strain gauges/sensors 190. The strain gauges 190 are attached to a pedal axle for the determining the orientation of force applied by a cyclist. Strain gauges 190 may be extensoresistive (piezoresistive) or extensoelectric (piezoelectric) devices and may be either uni-directional or bi-directional. Preferably, the strain gauges 190 are uni-axial piezoresistive strain gauges, such as the KFG-02-120-C1-11 strain gauge manufactured by KYOWA of Japan. Preferably, the gauges 190 are electrically coupled to a Wheatstone bridge signal conditioning circuit.

The signal conditioned outputs of the strain gauges 190 are electrically coupled to the controller 101 by connection 191. The connection may be a wired or wireless connection. The strain gauges 190 are mounted on the pedal axle which is fixed to a bicycle crank. As the bicycle crank rotates around the bottom bracket of the bicycle, electronic components mounted on the pedal axle can be connected by a wired connection to electric components mounted on the crank-arm, but any electronic components mounted on any other part of the bicycle must be connected by a wireless connection to the electronic components on the axle or crank-arm. In one embodiment, the strain gauges 190 are mounted on the pedal axle and are connected by wires to a module (not shown) mounted to the inside of the crank-arm. The module comprises signal conditioning, digital signal processing and wireless transmission circuitry. The pedal axle may also be provided with internal passages to allow the wires to extrude from the end of the axle at the inside of the crank-arm. The module calculates the resulting force/torque/power data and transmits the data wirelessly to a display/head unit.

Alternatively, the threaded end of the pedal axle may be extended by a cylindrical housing of slightly smaller diameter than the thread diameter (typically $9/16$ inch) which passes through the threaded aperture of the crank arm. The housing may contain the electronics mentioned above so as to remove the need for a wired connection to be reconnected each time a pedal was transferred to a new bicycle.

The methods described below can be implemented using the embedded controller 102 wherein the algorithms, equations and methods, to be described, can be implemented as one or more software application programs 133 executable within the embedded controller 102. Preferably, the processor 105 is a 16-bit digital signal processing microprocessor. The electronic device 101 is an effective and advantageous apparatus for implementing the described methods. In particular, with reference to FIG. 1B, the steps of the described methods are effected by instructions in the software 133 that are carried out within the controller 102. The software instructions may be formed as one or more code modules, each for performing one or more particular tasks. The software may also be divided into two separate parts, in which a first part and the corresponding code modules performs the described methods and a second part and the corresponding code modules manage a user interface between the first part and the user.

The software 133 is generally loaded into the controller 102 from a computer readable medium, and is then typically stored in the ROM 160 of the internal storage module 109, as illustrated in FIG. 1A, after which the software 133 can be executed by the processor 105. In some instances, the processor 105 may execute software instructions that are located in RAM 170. Software instructions may be located in RAM 170 by the processor 105 initiating a copy of one or more code modules from ROM 160 into RAM 170. Alternatively, the software instructions of one or more code modules may be pre-installed in a non-volatile region of RAM 170 by a manufacturer. After one or more code modules have been located in RAM 170, the processor 105 may execute software instructions of the one or more code modules.

As described herein, the application program 133 is typically pre-installed and stored in the ROM 160 by a manufacturer, prior to distribution of the electronic device 101. However, in some instances, the application programs 133 may be supplied to the user encoded on one or more CD-ROM (not shown) and read via the portable memory interface 106 prior to storage in the internal storage module 109 or in the portable memory 125. In another alternative, the software application program 133 may be read by the processor 105 from the network 120 or loaded into the controller 102 or the portable storage medium 125 from other computer readable media. Computer readable storage media refers to any storage medium that participates in providing instructions and/or data to the controller 102 for execution and/or processing. Examples of such storage media include floppy disks, magnetic tape, CD-ROM, a hard disk drive, a ROM or integrated circuit, USB memory, a magneto-optical disk, flash memory, or a computer readable card such as a PCMCIA card and the like, whether or not such devices are internal or external of the device 101. Examples of computer readable transmission media that may also participate in the provision of software, application programs, instructions and/or data to the device 101 include radio or infra-red transmission channels as well as a network connection to another computer or networked device, and the Internet or Intranets including e-mail transmissions and information recorded on Websites and the like. A computer readable medium having such software or computer program recorded on it is a computer program product.

The second part of the application programs 133 and the corresponding code modules mentioned above may be executed to implement one or more graphical user interfaces (GUIs) to be rendered or otherwise represented upon the display 114. Through manipulation of the user input device 113 (e.g., the keypad), a user of the device 101 and the application programs 133 may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers (not illustrated) and user voice commands input via the microphone (not illustrated).

FIG. 1B is a detailed schematic block diagram of the controller 102 comprising the processor 105 for executing the application programs 133, and the internal storage 109. The internal storage 109 comprises read only memory (ROM) 160 and random access memory (RAM) 170. The processor 105 is able to execute the application programs 133 stored in one or both of the connected memories 160 and 170. When the electronic device 102 is initially powered up, a system program resident in the ROM 160 is executed. The application program 133 permanently stored in the ROM 160 is sometimes referred to as "firmware". Execution of the firmware by the processor 105 may fulfil various functions, including processor management, memory management, device management, storage management and user interface.

The processor 105 typically includes a number of functional modules including a control unit (CU) 151, an arithmetic logic unit (ALU) 152 and a local or internal memory comprising a set of registers 154 which typically contain atomic data elements 156, 157, along with internal buffer or cache memory 155. One or more internal buses 159 interconnect these functional modules. The processor 105 typically also has one or more interfaces 158 for communicating with external devices via system bus 181, using a connection 161.

The application program 133 includes a sequence of instructions 162 though 163 that may include conditional branch and loop instructions. The program 133 may also include data, which is used in execution of the program 133. This data may be stored as part of the instruction or in a separate location 164 within the ROM 160 or RAM 170.

In general, the processor 105 is given a set of instructions, which are executed therein. This set of instructions may be organised into blocks, which perform specific tasks or handle specific events that occur in the electronic device 101. Typically, the application program 133 will wait for events and subsequently execute the block of code associated with that event. Events may be triggered in response to input from a user, via the user input devices 113, as detected by the processor 105. Events may also be triggered in response to other sensors and interfaces in the electronic device 101.

The execution of a set of the instructions may require numeric variables to be read and modified. Such numeric variables are stored in the RAM 170. The disclosed method uses input variables 171 that are stored in known locations 172, 173 in the memory 170. The input variables are processed to produce output variables 177 that are stored in known locations 178, 179 in the memory 170. Intermediate variables 174 may be stored in additional memory locations in locations 175, 176 of the memory 170. Alternatively, some intermediate variables may only exist in the registers 154 of the processor 105.

The execution of a sequence of instructions is achieved in the processor 105 by repeated application of a fetch-execute cycle. The control unit 151 of the processor 105 maintains a register called the program counter, which contains the address in ROM 160 or RAM 170 of the next instruction to be executed. At the start of the fetch execute cycle, the contents of the memory address indexed by the program counter is loaded into the control unit 151. The instruction thus loaded controls the subsequent operation of the processor 105, causing for example, data to be loaded from ROM memory 160 into processor registers 154, the contents of a register to be arithmetically combined with the contents of another register, the contents of a register to be written to the location stored in another register and so on. At the end of the fetch execute cycle the program counter is updated to point to the next instruction in the system program code. Depending on the instruction just executed this may involve incrementing the address contained in the program counter or loading the program counter with a new address in order to achieve a branch operation.

Each step or sub-process in the processes of the methods, algorithms or equations described below is associated with one or more segments of the application program 133, and is performed by repeated execution of a fetch-execute cycle in the processor 105 or similar programmatic operation of other independent processor blocks in the electronic device 101.

Calculating Torque and Power

Figure 2:
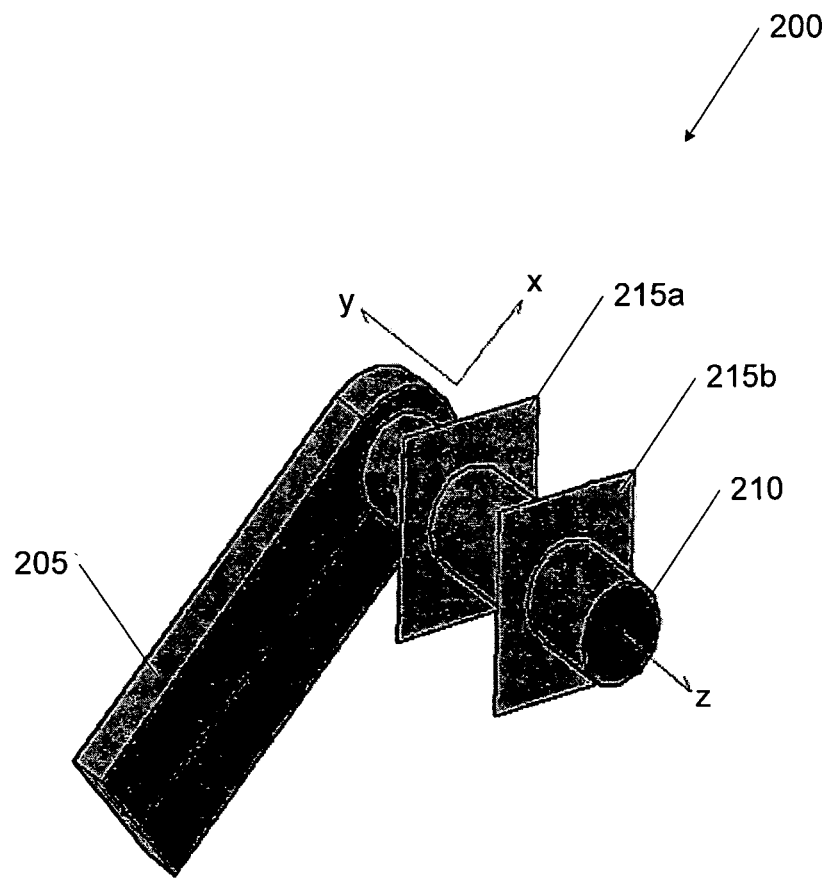
FIG. 2 shows a pedal used in conjunction with a bicycle.

FIG. 2 shows a bicycle pedal 200 comprising an axle 210 connected to a crank arm 205. While a bicycle is used as an example throughout this description, other pedal powered vehicles are also envisaged.

The pedal 200 comprises a pedal axle 210 mechanically coupled to a perpendicular crank arm 205. The pedal axle 210 and crank arm 205 form a cantilevered beam which is subject to orthogonal forces at planes 215a and 215b. Planes 215a and 215b coincide with the location of the bearings joining a pedal body (not shown) to the pedal axle 210.

The force components at planes 215a and 215b in the direction of rotation can be used to calculate the power and torque applied to the pedal. In other words, the torque and power applied to the pedal can be calculated from the y-axis force components of planes 215a and 215b; the y-axis force component being at right angles to the crank arm 205 as shown in FIG. 2. Generally, left and right pedals 200 are used to measure the power output and torque applied by each leg of the cyclist.

Calculating the Angle of the Applied Force

Figure 3A:
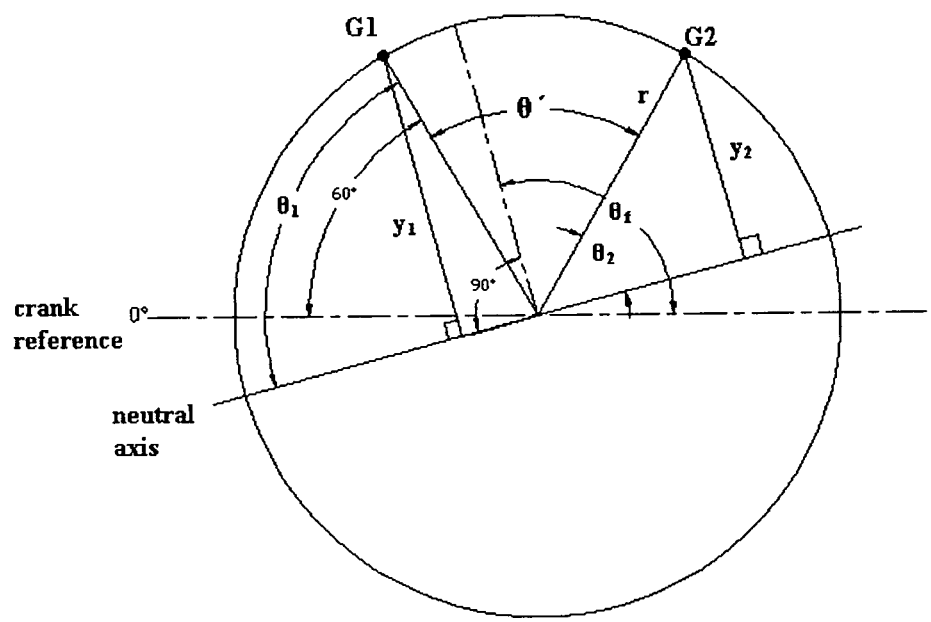
FIG. 3A shows a planar cross section of a circular beam subject to a pure bending load comprising two strain measuring points.

FIG. 3A shows a planar cross-section of a circular beam subject to a pure bending load. FIG. 3A shows two strain measurement points G1 and G2.

According to the theory of the mechanics of deformable bodies, a neutral plane (being a plane not subject to any stresses or strains) exists at the midpoint of the beam between the upper portion of the beam subject to tension and the lower portion of the beam subject to compression.

The calculation of the angular orientation (representing the angle of the applied force) of the neutral plane based on the ratio of strains at two points G1 and G2 comprises two equations:

$$\frac{y_2}{y_1} = \frac{\sin\theta_2}{\sin\theta_1} \text{ and,} \qquad \text{Equation 1}$$

$$\theta_1 + \theta_2 = 180° - \theta' \qquad \text{Equation 2}$$

Figure 6:
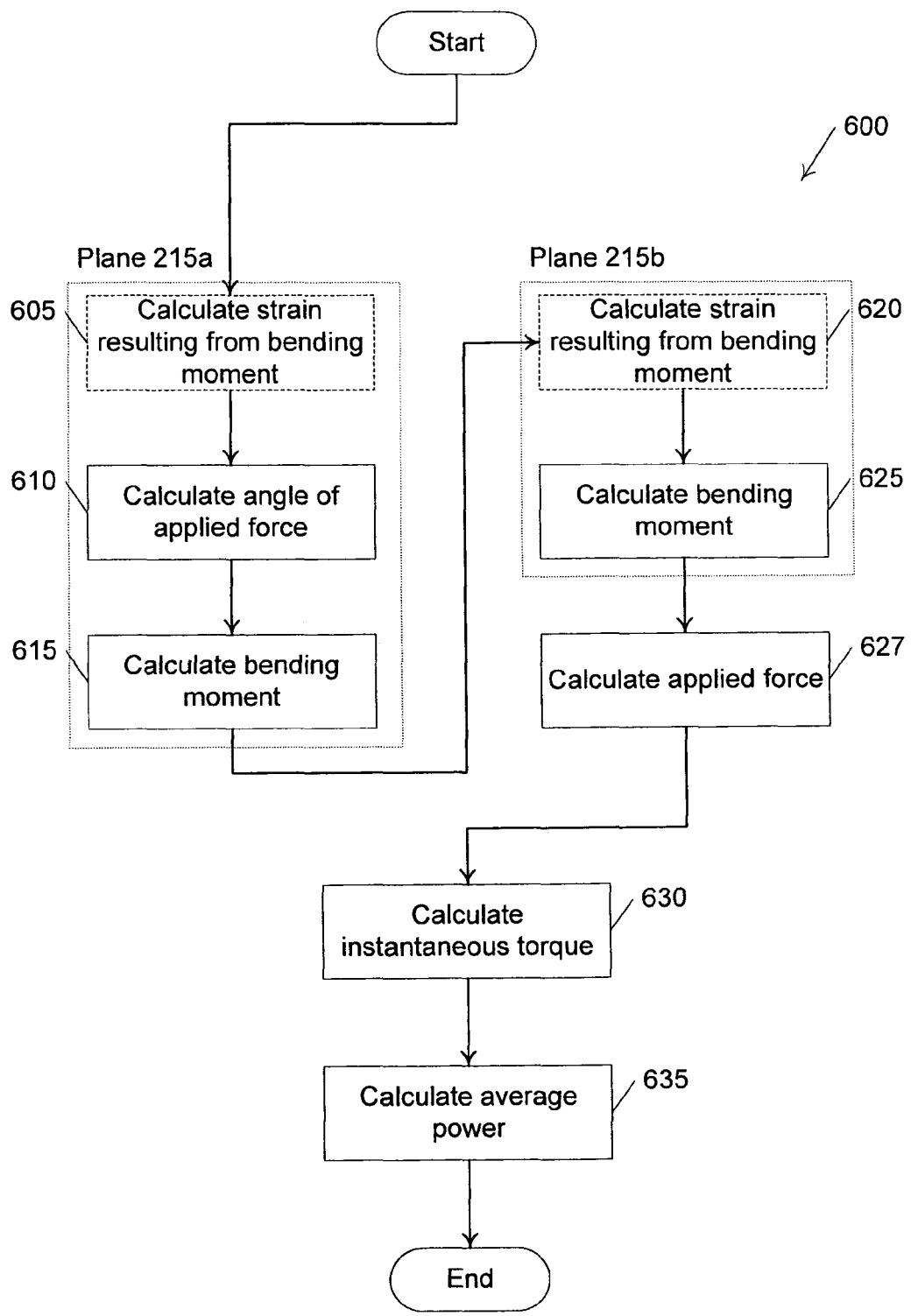
FIG. 6 shows a method for calculating the power and the torque applied to a pedal.

As described herein with reference to the method 600 described in FIG. 6, equations (1) and (2) can be solved either numerically or analytically.

Specifically, where angle $\theta_2$ is expressed as function of the ratio $y_2/y_1$ for a known angular separation of G1 and G2 being $\theta'$, equations (1) and (2) can be evaluated numerically. Alternatively, where the strain gauges 190 are placed 90° apart, equations (1) and (2) can be evaluated analytically.

An iterative solution can be difficult to implement in real time at current processor speeds.

Numerical Solution—Calculating the Numerical Polynomial Relationship Between the Angular Orientation of the Neutral Plane and Ratio of Strains in Two Gauges with a Known Angular Separation As strain gauges have finite size, it is impractical to measure strain at a point. For example, where a gauge has a width of 1.1 mm and is attached to a shaft of 18 mm in diameter, the angle over which the gauge would measure strain is:

$$\frac{1.1}{18\pi} \times 360 = 7° \qquad \text{Equation 3}$$

In other words, such a gauge would cover an arc of ±3.5° about the position at which the gauge is mounted. As such, since $y = r\sin\theta$, where r is the radius of the beam, the average strain at the gauge with respect to y is therefore:

$$y_1 = r\sin(\theta + 3.5°) \qquad \text{Equation 4a}$$

$$y_2 = r\sin(\theta - 3.5°) \qquad \text{Equation 4b}$$

$$\varepsilon_{ave.} = \frac{\int_{y_2}^{y_1} \frac{MY}{IE} dy}{y_1 - y_2} \qquad \text{Equation 5}$$

Now, evaluating the integral:

$$\varepsilon_{ave.} = \frac{M}{IE} \times \frac{\left[\frac{y^2}{2}\right]_{y_2}^{y_1}}{y_1 - y_2} \qquad \text{Equation 6}$$

Therefore, with reference to a unit radius:

$$\frac{G_2}{G_1} = \frac{\left(\frac{\sin^2(\theta_2 + 3.5°) - \sin^2(\theta_2 - 3.5°)}{2(\sin(\theta_2 + 3.5°) - \sin(\theta_2 - 3.5°))}\right)}{\left(\frac{\sin^2(\theta_1 + 3.5°) - \sin^2(\theta_1 - 3.5°)}{2(\sin(\theta_1 + 3.5°) - \sin(\theta_1 - 3.5°))}\right)} \qquad \text{Equation 7}$$

Figure 3B:
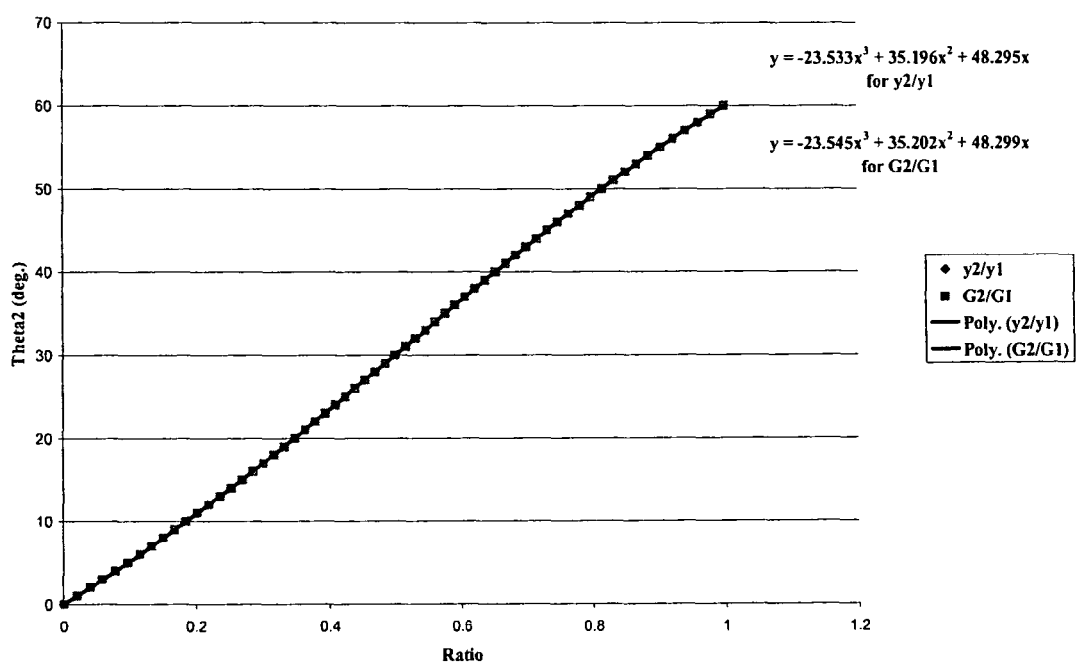
FIG. 3B shows a plot of the numerical polynomial relationship for determining the angular orientation of a neutral plane based on a ratio of strains in two gauges with a known angular separation

Equations (7) and (2) can be evaluated numerically to plot $\theta_2$ as a function of $G_2/G_1$. For example FIG. 3B displays such a plot for $y_2 \le y_1$, $\theta_2 \le \theta_1$, for both the point strain and average gauge strain ratios discussed above.

Polynomial curves of varying order are fitted to this plot in order to establish a numerical relationship of sufficient accuracy. Data-point density on the plots being commensurate with the desired accuracy of $\theta_2$ for both the point strain, and average gauge strain cases. In other words, when fitting a curve to a data set the accuracy of the fitted curve to any interpolated points (data points between those already known) increases as the number of known data points increases. That is, if only two data points are known then a line can be fitted to them perfectly and the regression coefficient ($r^2$) value returned from the statistical regression technique used to fit the line to the two points would be 1, indicating a perfect fit however it is very possible that any intermediate datapoints do not fit this line. In this case, if it is desired for the fitted polynomial curve to be 100% accurate at a 1° resolution, then the data point density needs to be every 1° prior to fitting the curve. If the data point density were only every 5° then the curve is only 100% accurate with a 5° resolution. The order of the polynomial curves of best fit can be increased until a regression coefficient ($r^2$) of 1 is obtained indicating no discrepancy between the numerical relationship and the analytical values at the desired resolution depending on the desired level of accuracy.

As such, the numerical polynomial relationship can be used to calculate the angular orientation of the neutral plane to within the desired resolution based on a ratio of strains in two gauges with a known angular separation.

Numerical Solution—Calculating the Numerical Polynomial Relationship Between the Angular Orientation of the Neutral Plane and Ratio of Strains in Four Gauges with a Known Angular Separation Similarly, in the manner described above, the angular orientation of the neutral plane can be determined based on a ratio of four strains with a known angular separation.

Figure 4:
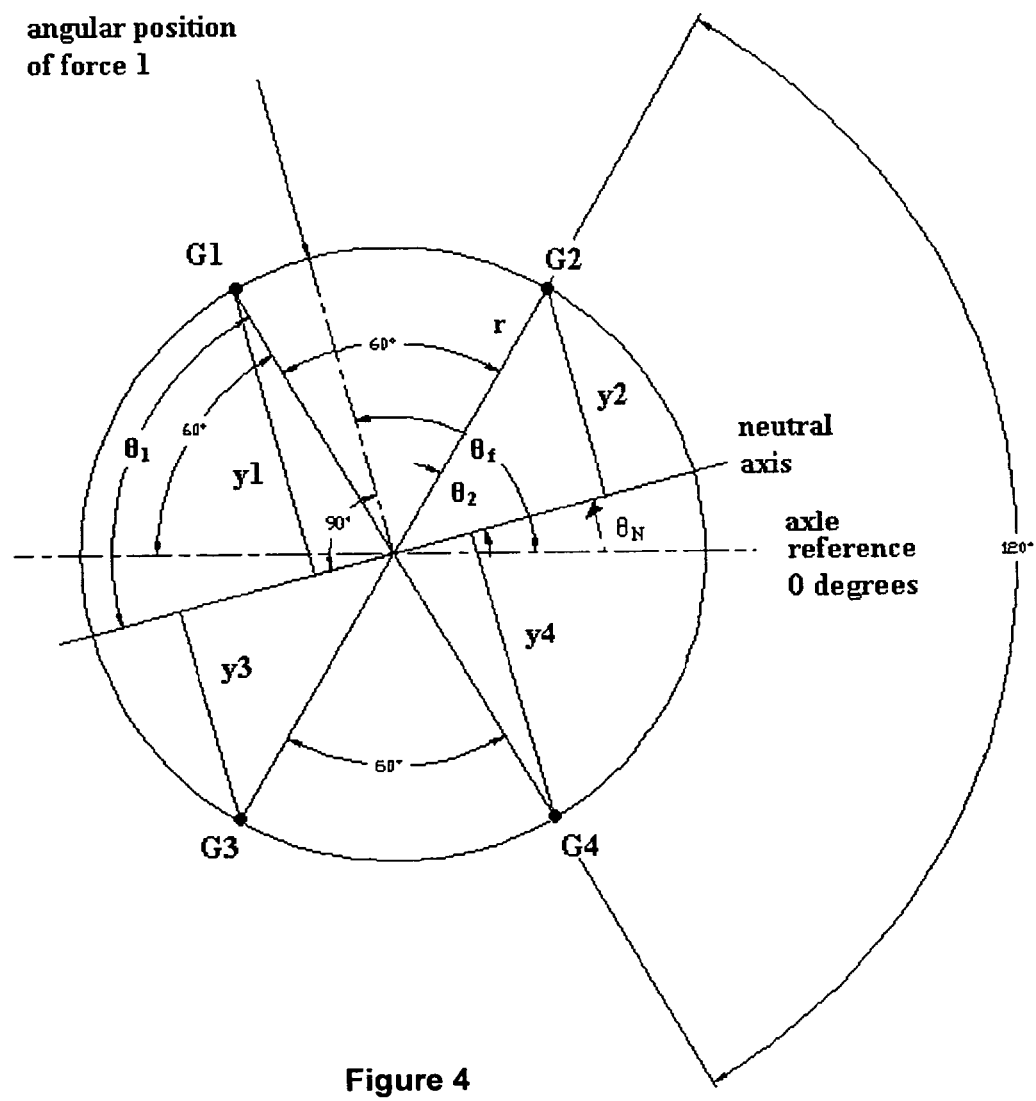
FIG. 4 shows a planar cross section of a circular beam subject to a pure bending load comprising four strain measuring points.

FIG. 4 shows a planar cross-section of a circular beam subject to a pure bending load. FIG. 4 shows four strain measurement points G1 to G4. G1 to G4 are arranged such that any two gauges are either 60° or 120° apart. The algorithm to calculate the orientation of the applied force is given in Appendix A in which a series of conditional statements are used to determine in which of eight segments the applied force lies (e.g. case 1 through 4). The algorithm applies the numerical polynomial solution to calculate the exact orientation of the force in that segment.

First Embodiment Utilising a Numerical Solution for Six Gauges and Two Planes

Figure 5:
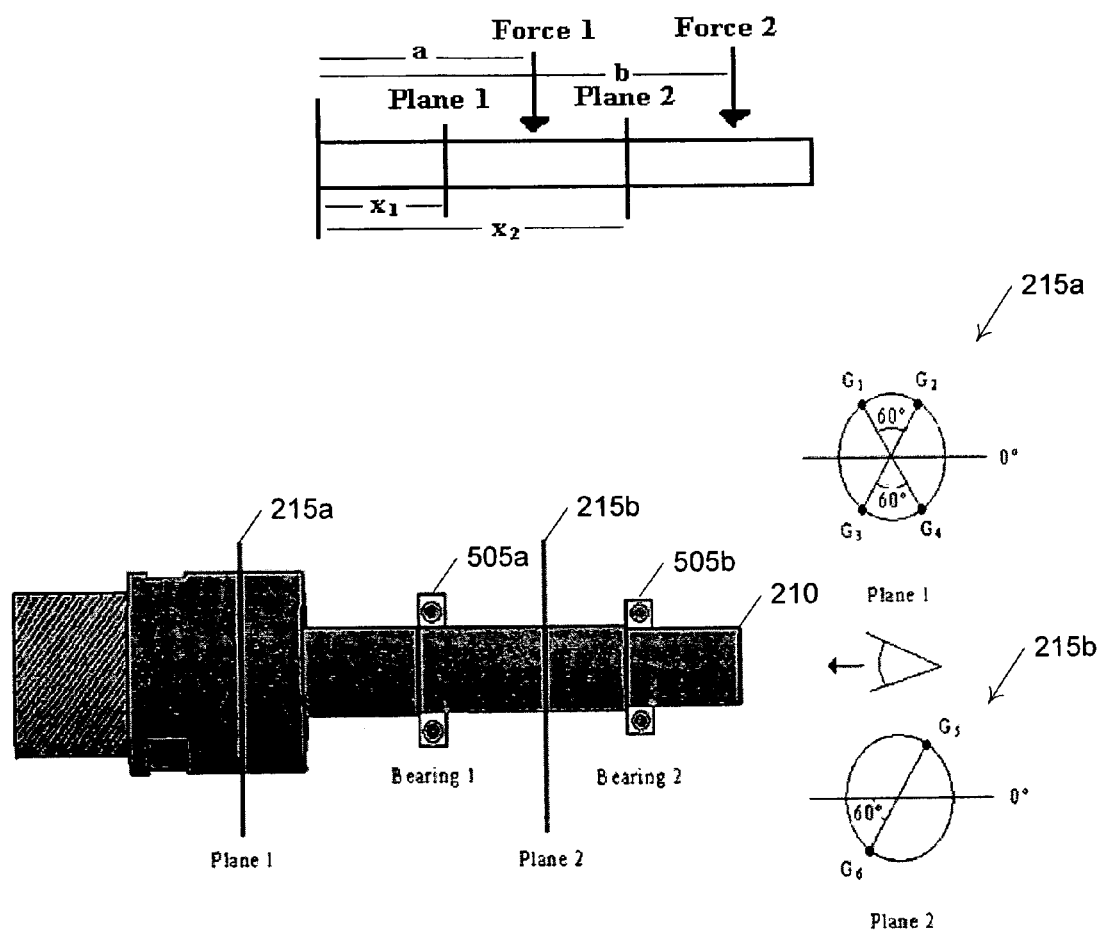
FIG. 5 shows a first embodiment comprising a pedal axle connected to a pedal body.

FIG. 5 shows the pedal axle 210 connected to a pedal body (not shown) by bearings 505. The pedal axle 210 is provided with the strain gauges 190 on planes 215*a* and 215*b*.

In order to mount the strain gauges 190, the mounting surface is first degreased with Vishay CSM-2 degreaser, then wiped clean, whereafter it is subjected to a wet abrasion using a very fine grit sandpaper and Vishay M-prep conditioner-A until the mounting surface displays no marks or scratches. Grid lines used to locate the strain gauges are burnished onto the mounting surface using a ballpoint pen. The mounting surface is then wiped clean with Vishay M-prep conditioner-A, after which the mounting surface is wiped with Vishay M-prep neutralizer-A. The gauge 190 is located by holding the gauge 190 with Vishay PCT-2M clear tape and aligning it with the burnished marks. Finally the gauge 190 is glued in place using manufacturer's (Kyowa's) recommended glue CC-33A. Lead wire tabs are glued in place alongside the gauge 190 installation and lead wires soldered to the tabs using Vishay 361A-20R solder.

In this first embodiment, six gauges 190 are employed. Four gauges 190 are located on the first plane 215*a* where each pair of gauges 190 are offset by 60° as shown in FIG. 5. Gauges G1 to G4 are configured in a quarter Wheatstone bridge formation. Two gauges 190 are located on the second plane 215b, being offset at 180° and configured in quarter bridge formation.

The Wheatstone bridge configuration is a well understood technique for translating very slight changes in resistance to changes in voltage. In this first embodiment all the gauges 190 are configured in quarter bridge circuits. Each gauge 190 provides an output independent of the other gauges 190 so as to allow the force in the z-plane to be calculated based on the difference in absolute magnitude of output between two diametrically opposed gauges 190 as described below.

FIG. 6 shows a flow-charted method 600 for calculating the power and the torque applied to a pedal from the strain measurements of gauges G1-G6.

The method 600 comprises two branches, with steps 605 to 615 being performed with respect to the first plane 215a and steps 620 to 625 being performed with respect to the second plane 215b.

Figure 8:
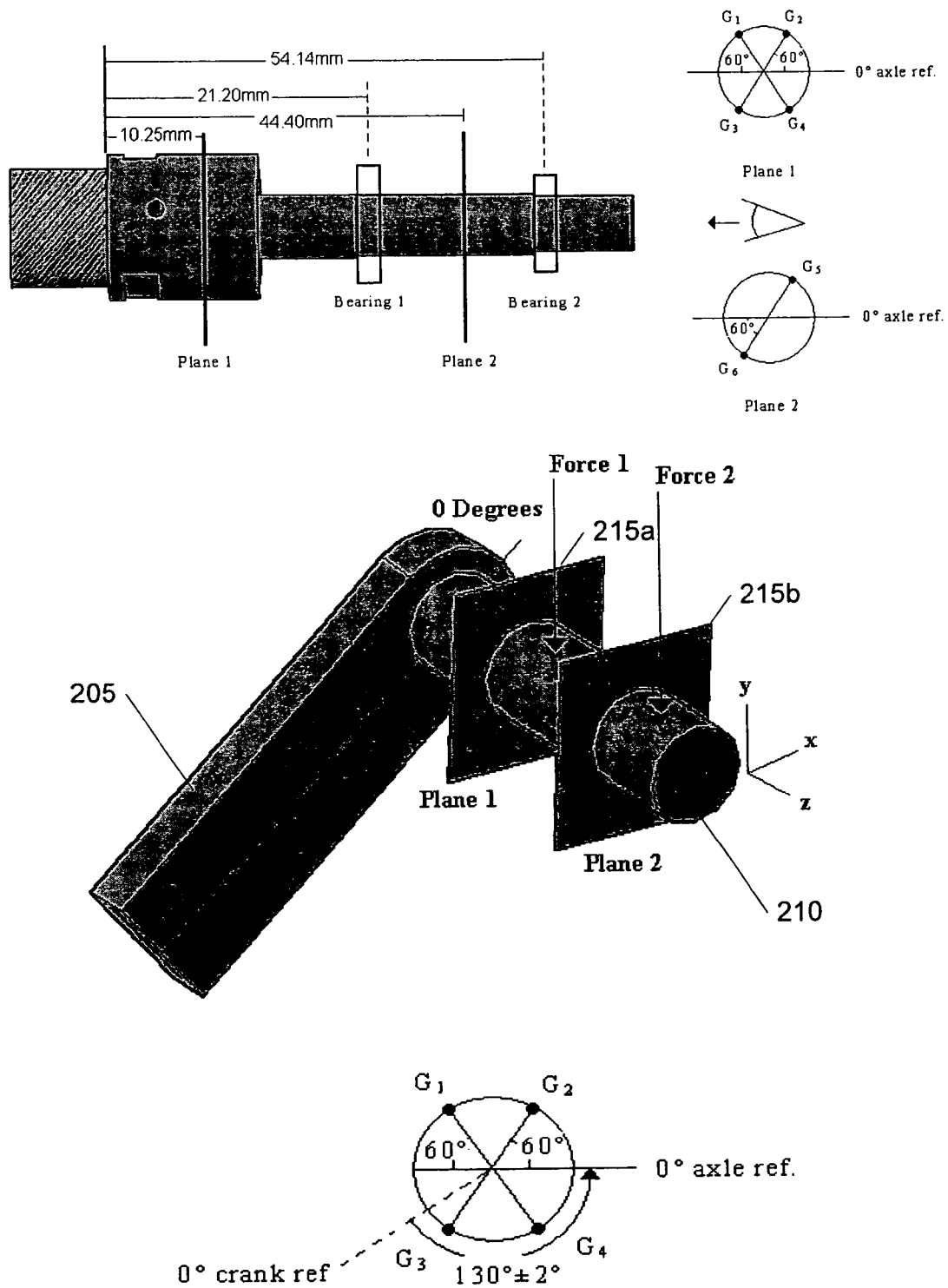

Note that for method 600, any difference between the 0° reference of the pedal axle 210 and the 0° reference of the crank arm 205 can be used as a correctional constant in the calculations that follow. For example, in the specific embodiment shown in FIG. 8, the orientation of the strain gauge 190 location varies in relation to the axis of the crank arm 205 when the pedal axle 210 is threaded onto the crank arm 205. Therefore, the angle between the pedal axle 0° reference and the crank arm 0° reference is measured and accounted for in the calculations below.

The method 600 begins at step 605 where the strain resulting from the bending moment is calculated. For a circular beam experiencing bending, the strain at any two diametrically opposite points on the same plane is equal but opposite in sign. Therefore the component of force applied by the cyclist in the lateral z-axis direction can be calculated from the difference between the magnitudes of the strains diametrically opposite each other.

Therefore the total magnitude of the strain on the axle 210 in the z-axis direction is:

$$\varepsilon_2 = \left| \frac{(|G1| - |G4|) + (|G2| - |G3|)}{4} \right| \qquad \text{Equation 8}$$

The direction of the z-axis strain can be determined by the following algorithm:

```
If G₁ > G₄ then
    If |G₁| > |G₄| then ε_z = ε_z  // tensile axial strain //
    Elseif |G₁| < |G₄| then ε_z = -ε_z  // compressive axial strain //
Endif
If G₁ < G₄ then
    If |G₁| > |G₄| then ε_z = -ε_z  // tensile axial strain //
    Elseif |G₁| < |G₄| then ε_z = ε_z  // compressive axial strain //
Endif
```

Therefore the strain in gauges G1 through G4 resulting from the bending moment is:

$G_1 = G_1 - \epsilon_z$ $G_2 = G_2 - \epsilon_z$ $G_3 = G_3 - \epsilon_z$ $G_4 = G_4 - \epsilon_z$ \qquad Equation 9

Assuming a linear elastic relationship between stress and strain for the pedal axle material, Hooke's law states (where E is the elastic modulus of the material, $\epsilon$ is measured strain and $\sigma$ is stress):

$$\sigma = E\epsilon \qquad \text{Equation 10}$$

The stress of bending $\sigma$ is related to the bending moment and perpendicular height from the neutral axis for a beam in pure bending by the flexure formula (where M is the bending moment Y is the height above the neutral axis and I is the second moment of area of the beam):

$$\sigma = \frac{MY}{I} \qquad \text{Equation 11}$$

Since I is constant, and all the gauges 190 in one plane are subject to the same bending moment:

$$\frac{\sigma_1}{\sigma_2} = \frac{\varepsilon_1}{\varepsilon_2} = \frac{y_1}{y_2} \qquad \text{Equation 12}$$

At step 610, the angle of the applied force relative to the crank ($\theta_f$) is calculated. Using the strain values corrected for the axial strain component resulting from equation (9), the angle of the applied force relative to the crank ($\theta_f$) can be found as follows (all angles are measured positive CCW from the 0° crank reference):

Case 1: $G_1 > G_4$ && $G_2 > G_3$

If $G_1 > G_2$ then $\theta_2 = -23.533 \left(\frac{G_2}{G_1}\right)^3 + 35.196 \left(\frac{G_2}{G_1}\right)^2 + 48.295 \left(\frac{G_2}{G_1}\right)$ $\theta_{neutralaxis} = 60 - \theta_2$ $\theta_f = \theta_{neutralaxis} + 90 = 140 - \theta_2$ Elseif $G_1 < G_2$ then $\theta_1 = -23.533 \left(\frac{G_1}{G_2}\right)^3 + 35.196 \left(\frac{G_1}{G_2}\right)^2 + 48.295 \left(\frac{G_1}{G_2}\right)$ $\theta_{neutralaxis} = -(60 - \theta_1)$ $\theta_f = \theta_{neutralaxis} + 90 = \theta_1 + 30$ Case 2: $G_1 > G_4$ && $G_2 < G_3$ If $G_1 > G_3$ then $\theta_3 = -6.5551 \left(\frac{G_3}{G_1}\right)^3 - 26.256 \left(\frac{G_3}{G_1}\right)^2 + 49.713 \left(\frac{G_3}{G_1}\right)$ $\theta_{neutralaxis} = 60 + \theta_3$ $\theta_f = \theta_{neutralaxis} + 90 = 140 - \theta_3$ Elseif $G_1 < G_3$ then $\theta_1 = 6.5551 \left(\frac{G_1}{G_3}\right)^3 - 26.256 \left(\frac{G_1}{G_3}\right)^2 + 49.713 \left(\frac{G_1}{G_3}\right)$ $\theta_{neutralaxis} = 120 - \theta_1$ $\theta_f = \theta_{neutralaxis} + 90 = 210 + \theta_1$ Case 3: $G_1 < G_4$ && $G_2 > G_3$ If $G_2 > G_4$ then -continued $$\theta_4 = -6.5551\left(\frac{G_4}{G_2}\right)^3 - 26.256\left(\frac{G_4}{G_2}\right)^2 + 49.713\left(\frac{G_4}{G_2}\right)$$

$\theta_{neutralaxis} = -60 - \theta_4$ $\theta_f = \theta_{neutralaxis} + 90 = 30 - \theta_4$ Elseif $G_2 < G_4$ then $$\theta_2 = 6.5551\left(\frac{G_2}{G_4}\right)^3 - 26.256\left(\frac{G_2}{G_4}\right)^2 + 49.713\left(\frac{G_2}{G_4}\right)$$

$\theta_{neutralaxis} = -120 + \theta_2$ $\theta_f = \theta_{neutralaxis} + 90 = -30 + \theta_2$ Case 4: $G_1 < G_4$ && $G_2 < G_3$ If $G_3 > G_4$ then $$\theta_4 = -23.533\left(\frac{G_4}{G_3}\right)^3 + 35.196\left(\frac{G_4}{G_3}\right)^2 + 48.295\left(\frac{G_4}{G_3}\right)$$

$\theta_{neutralaxis} = -60 + \theta_4$ $\theta_f = \theta_{neutralaxis} + 90 = 30 + \theta_4$ Elseif $G_3 < G_4$ then $$\theta_3 = -23.533\left(\frac{G_3}{G_4}\right)^3 + 35.196\left(\frac{G_3}{G_4}\right)^2 + 48.295\left(\frac{G_3}{G_4}\right)$$

$\theta_{neutralaxis} = 60 - \theta_3$ $\theta_f = \theta_{neutralaxis} + 90 = 150 - \theta_3$ At step 615 the bending moment of plane 215a is calculated. The bending moment $M_1$ in plane 215a is calculated based on the calculated angle $\theta_i$, and the corresponding strain gauge value $G_i$ (where the subscript i denotes the number of gauge 190 selected by the conditional statements in the above algorithm), by combining equations (10) and (11). In order to mitigate error arising from gauge 190 placement uncertainty and signal noise, for an instantaneous sample of the dynamic strain signals, $G_i$ is chosen as the strain gauge 190 highest above the neutral plane based on the calculated value of $\theta_{neutralaxis}$.

$$EG_i = \frac{M_i Y_i}{I} \qquad \text{Equation 13}$$

For a circular cross section, I (second moment of area) is $$I = \frac{\pi d^4}{64} \qquad \text{Equation 14}$$

and since $$Y_i = r \sin \theta_i \qquad \text{Equation 15}$$

only $M_1$ is unknown and can be solved for.

At step 620, the strain resulting from the bending moment is calculated with respect to the second plane 215b. The portion of axial strain transmitted to this plane is calculated as follows:

$$\varepsilon_{z'} = \left|\frac{(|G_5| - |G_6|)}{2}\right| \qquad \text{Equation 16}$$

The direction of the z strain can be determined by the following algorithm.

```
If G_5 > G_6 then
    If |G_5| > |G_6| then ε_z = ε_z  // tensile axial strain //
    Elseif |G_5| < |G_6| then ε_z = -ε_z  // compressive axial strain //
    Endif
If G_5 < G_6 then
    If |G_5| > |G_6| then ε_z = -ε_z  // tensile axial strain //
    Elseif |G_5| < |G_6| then ε_z = ε_z  // compressive axial strain //
    Endif
```

Therefore the corrected strain (resulting from the bending moment only) is:

$$G_5 = G_5 - \varepsilon_{z'}$$

$$G_6 = G_6 - \varepsilon_{z'} \qquad \text{Equation 17}$$

At step 625, the bending moment at plane 215b is calculated as follows:

If $G_5 > G_6$ then $$Y_5 = r\sin(60 + \theta_{neutralaxis})$$

$$M_2 = \frac{EG_5 I}{Y_5}$$

If $G_5 < G_6$ then $$Y_6 = r\sin(60 + \theta_{neutralaxis})$$

$$M_2 = \frac{EG_6 I}{Y_6}$$

At step 627, once the instantaneous bending moments in each measurement plane and the instantaneous angular orientation of the neutral plane and therefore the instantaneous angular orientation of the resultant force(s) in the xy plane are known, based on the magnitudes of strain the instantaneous force(s) transmitted by the cyclist through the pedal body and bearings to the pedal axle 210 may be calculated based on calibration of the strain gauges against known loads/forces for a specific embodiment.

Specifically, Once $M_1$ and $M_2$ (the bending moments in the respective strain gauge containing plane 215a and plane 215b) are known, and presuming that the distance to each measurement plane and force application plane is known from the pedal axle design (i.e. distances $x_1$ $x_2$ a b are all known). The forces $F_1$ and $F_2$ are calculated as follows. A consideration of the bending moment equations for $0 \le x \le a$ produces the result $$M_1 = F_1(a - x_1) + F_2(b - x_1) \qquad \text{Equation 20}$$

And for $a \le x \le b$ $$M_2 = F_2(b - x_2) \qquad \text{Equation 21}$$

Solving equations 20 and 21 simultaneously allows forces $F_1$ and $F_2$ to be found.

Figure 7:
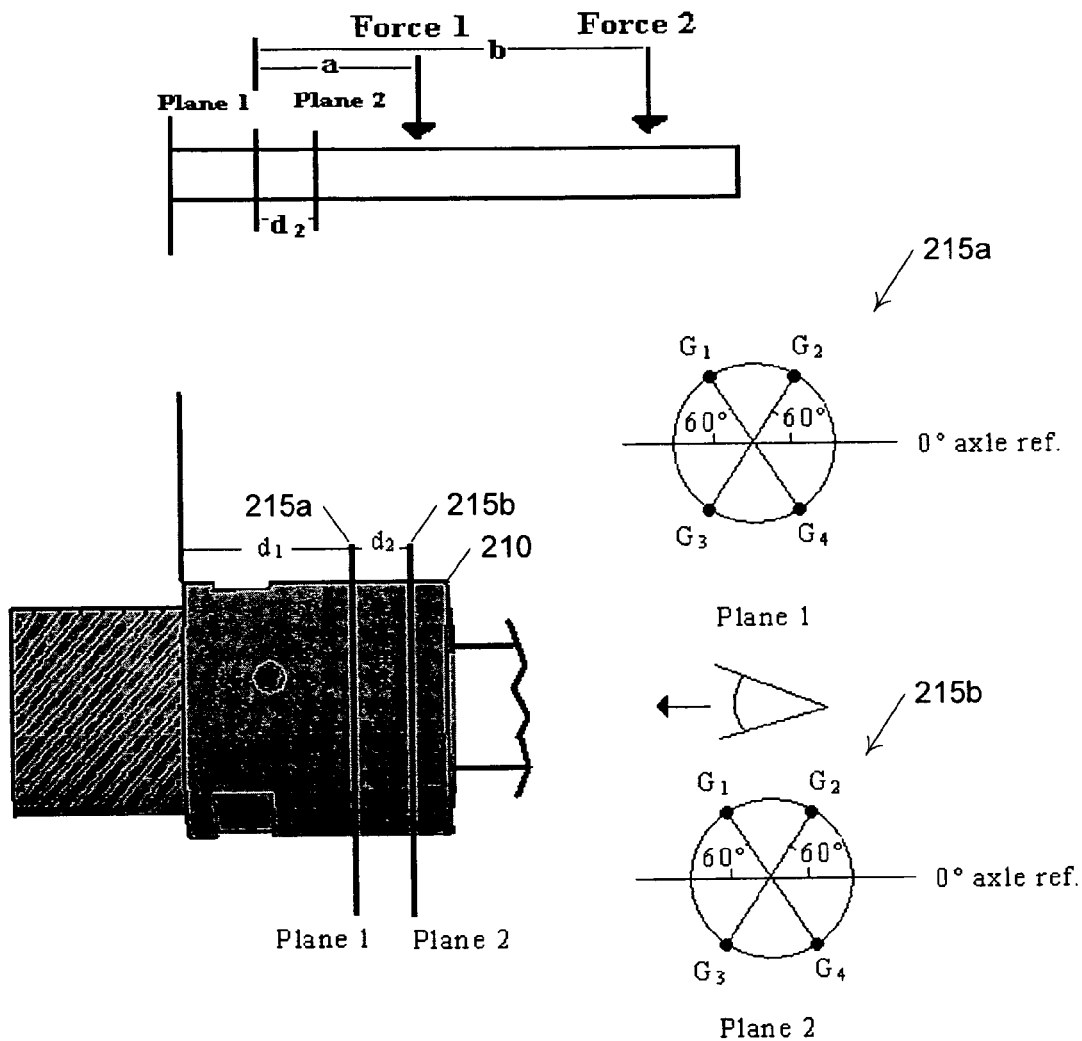
FIGS. 7 and 8 show specific embodiments comprising a pedal axle connected to a pedal body.

By way of another example, for the specific embodiment given in FIG. 7, once more $M_1$ and $M_2$ have been calculated for strain gauge planes 215a and 215b respectively and as distances $d_2$, a and b are known, the bending moments in the respective strain gauge containing plane 215a and plane 215b is calculated as:

$$M_1 = F_1(a) + F_2(b)$$

$$M_2 = F_1(a - d_2) + F_2(b - d_2)$$

Once more these two equations can be solved simultaneously to determine $F_1$ and $F_2$ The total resultant force in the XY plane applied by the cyclist is therefore $$F_{total} = F_1 + F_2$$

Now, the component of the total force normal to the crank 205 is calculated according to the following algorithm:

```
If 0 <= θ_F <= 90 Then
    F_norm = F_total 1 * Sin θ_F
ElseIf 90 < θ_F <= 180 Then
    F_norm = F_total * Sin(180 – θ_F)
ElseIf 180 < θ_F <= 270 Then
    F_norm = –F_total * Sin(θ_F – 180)
ElseIf 270 < θ_F <= 360 Then
    F_norm = –F_total * Sin(360 – θ_F)
End If
```

At step 630, the instantaneous torque is calculated. The instantaneous torque may be calculated using the instantaneous force y component perpendicular to the crank 205. Therefore for a known crank length ($L_c$) the instantaneous torque is:

$$T_{inst} = F_y * L_c \qquad \text{Equation 18}$$

Note that since the pedal axle 210 is fixed relative to the crank 205, a positive torque will only occur if $0 \le \theta_F \le 180$. A positive torque (propelling the cyclist forward) is therefore distinguished from a negative torque.

At step 635, the average power output is calculated. Calculation of the average power output requires the product of the instantaneous torque and the instantaneous angular velocity (i.e. instantaneous power) to be known over some averaging interval. The average power over one pedal stroke is obtained by summing the instantaneous power obtained at each sample interval and dividing by the number of samples:

$$P_{average} = \frac{\sum_{i=1}^{n} P_i}{n} \qquad \text{Equation 19}$$

The instantaneous angular speed is taken to be influenced by the inertia of bicycle drive-train and the cyclist's legs, i.e. it does not change appreciably over the course of one pedal stroke It is therefore possible to calculate the average angular velocity over one pedal revolution (this is equivalent to the cyclists cadence) and assume that this value is equivalent to the instantaneous angular velocity throughout the pedal stroke. The time that one pedal revolution takes can be measured by either tracking the value of $\theta_F$ as it passes through a full 360° or by using a magnetic switch (such as a reed switch such as is used in cycle computers for measuring speed or cadence) that closes once per pedal revolution.

The instantaneous change in $\theta_F$ is not indicative of the instantaneous angular velocity of the crank arm. $\theta_F$ may vary to a small degree, relative to the ground, over the course of one pedal stroke. This can be observed in clock diagrams, indicating the relative orientation of the crank, pedal and pedalling force for a single pedal stroke, as presented in Sanderson D. 1991, The Influence of Cadence and Power Output on the Biomechanics of Force Application During Steady Rate Cycling in Competitive and Recreational Cyclists, *Journal of Sport Sciences* vol. 9 no. 2 pp 191-203.

For each pedal stroke the following algorithm can be implemented in order to calculate the average power output for one pedal over one pedal stroke.

```
//initialize variables//
n = 0, m=0, PSum = 0
//calculation of average angular velocity for one pedal-stroke//
Do While θ_F > 0
    θ_F = θ_F(sample 'n')
    n = n + 1
Loop
Ave = (2 * Pi) / (0.01 * n) //average angular velocity over one pedal stroke in rad/s assuming sampling at 100Hz//
//Calculate the average power over one pedal stroke//
Do While m < n
    torque = torque(sample 'm')
    PSum = PSum + (torque * Ave)
    m = m + 1
Loop
PAverage = PSum / m //The average power output over one pedal stroke//
```

Second Embodiment Utilising a Numerical Solution for Eight Gauges and Two Planes In the manner described above, the steps of the method 600 may also be applied to calculate the power and torque for a second embodiment as shown in FIG. 7 in which each plane 215 comprises four strain gauges 190 configured in a half bridge formation. The strain gauges in each plane which are diametrically opposed comprise the two varying elements in one half bridge. A difference in this second embodiment over the first is that the axial strain is cancelled within the two element varying half bridge, and therefore the force in the z direction cannot be calculated.

Analytic Solution

As mentioned above it is possible to use an analytical solution to calculate the angular orientation of the neutral plane based on the ratio of strains at two points G1 and G2 if points G1 and G2 are placed 90° apart.

Figure 9:
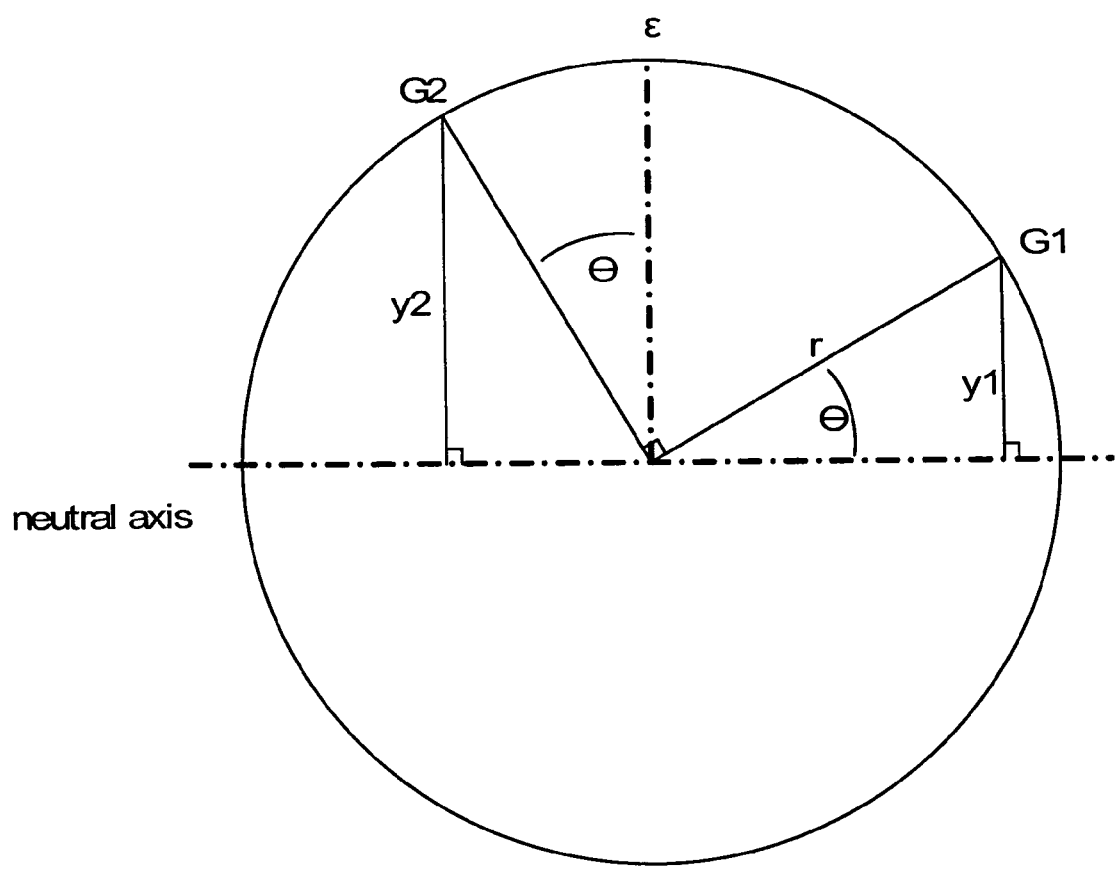
FIG. 9 shows two strain gauges placed at right angles.

FIG. 9 shows two strain gauges G1 and G2 placed at right angles. Such an arrangement allows for an analytical solution to be used to calculate the magnitude and angle of the strain relative to gauge placement. In FIG. 9, G1, G2 are the strain gauge measured values, r is the radius of the gauge placement surface, y1 and y2 are the displacement of the gauges from the neutral axis, c is the maximum magnitude of strain in any plane and $\ominus$ is the angle of gauge G1 to neutral axis.

Taking G1 to be the gauge with the lowest reading (i.e. $\ominus < 45°$), the measured strain increases linearly with distance from the neutral axis such that $G1/y1=G2/y2=\epsilon/r$. As such, $y2/r=G2/\epsilon$ and $y1/r=G1/\epsilon$. Now, since $y1=r \sin \ominus$ and $y2=r \cos \ominus$, $G1=\epsilon \sin \ominus$ and $G2=\epsilon \cos \ominus$ therefore $\epsilon^2=G1^2+G2^2$.

Figure 10:
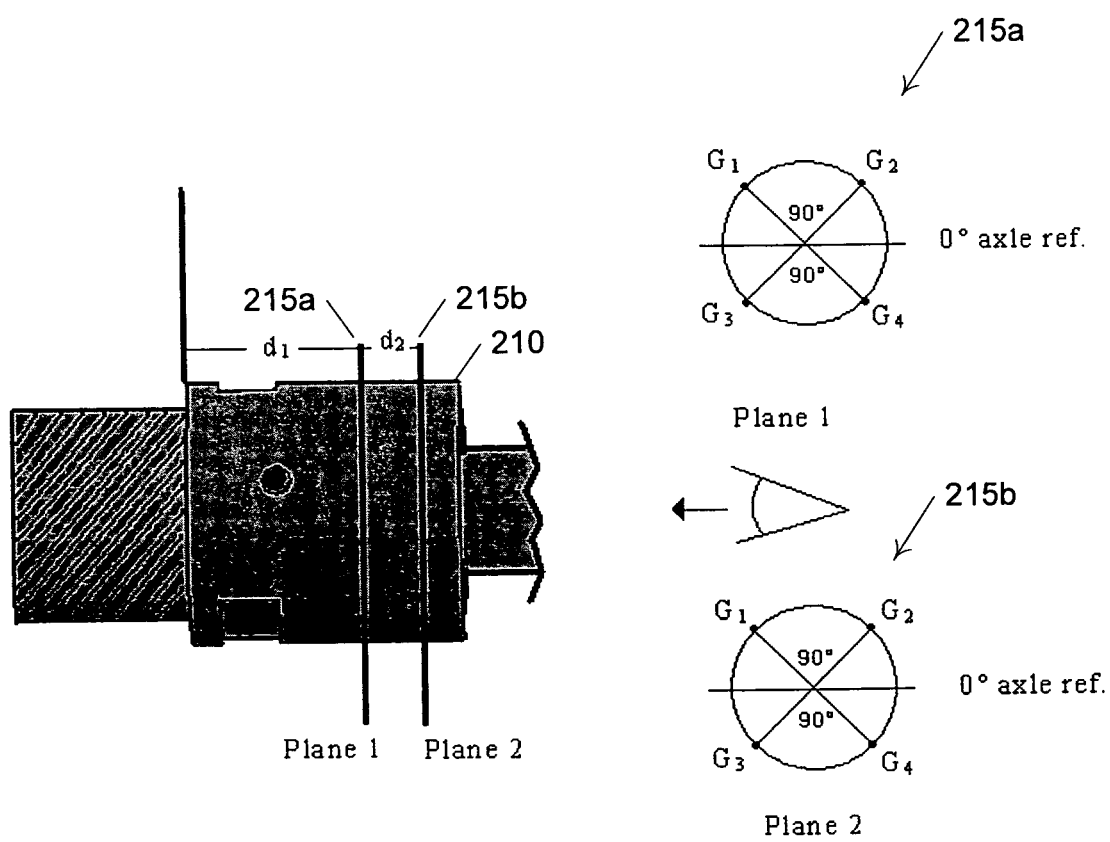
FIG. 10 shows a specific embodiment comprising two planes wherein each plane comprises four strain gauges placed 90° apart.

As such, the strain magnitude can be calculated as $\epsilon = \sqrt{(G1^2+G2^2)}$ The angle to the neutral plane can be calculated as $\ominus = \text{atan}(G1/G2)$ Third Embodiment Utilising an Analytic Solution for Eight Gauges and Two Planes FIG. 10 shows an embodiment comprising two planes 215a and 215b, each plane 215 comprising four gauges 190 placed 90° apart. In each plane 215, G1 and G4 are diametrically opposite, G2 and G3 are diametrically opposite and G2 is 45° from the 0° axle ref positive CCW.

The steps of the method 600 for calculating the angle of the applied force are now given. In plane 215a and 215b, G1 and G4 are connected in a half bridge (B1). A positive output of this bridge indicates that G1 is in tension. In plane 215a and 215b, G2 and G3 are also connected in a half bridge (B2). A positive output of this bridge indicates that G2 is in tension.

The method 600 starts at step 605. As a half bridge configuration is used, there is no strain in the z-direction to calculate because the output of the half bridge represents the full bending strain. As such the strain resulting from the bending moment is essentially the output of the Wheatstone bridge obtained by converting the strain induced resistance change in the gauge/bridge hardware into a suitable digitally sampled signal.

At step 610, the angle of applied force is calculated according to the analytical solution, rather than the numerical solution. The segment in which the applied force lies is determined using a series of conditional statements that discriminate which gauges 190 are in tension and which gauges 190 are in compression based on bias of output about the 0 reference (i.e. a positive or negative voltage if 0 volts is taken as a reference) and which gauges 190 are higher above the neutral plane and which gauges 190 are lower based on difference in magnitude. Then, for the gauge 190 closest to the neutral plane, the angle to the neutral plane is calculated as Θ=atan (G1/G2) and the maximum strain is ε=√(G1²+G2²).

Specifically, where θF is the angle from the axle 0 reference to the applied force in degrees positive counterclockwise (CCW):

Case 1 B1>0 && B2>0
Case 2 B1>0 && B2<0
Case 3 B1<0 && B2>0
Case 4 B1<0 && B2<0
For case 1

| |
|---|
| If B1 > B2 then |
| θ = atan (B2/B1) |
| θF = 135 − θ |
| Elseif B1 < B2 then |
| θ = atan (B1/B2) |
| θF = 45 + θ |

For case 2

| |
|---|
| B2 = abs (B2) //working with magnitude |
| If B1 > B2 then |
| θ = atan (B2/B1) |
| θF = 135 + θ |
| Elseif B1 < B2 then |
| θ = atan (B1/B2) |
| θF = 225 − θ |

For case 3

| |
|---|
| B1 = abs (B1) //working with magnitude |
| If B1 > B2 then |
| θ = atan (B2/B1) |
| θF = θ − 45 |
| Elseif B1 < B2 then |
| θ = atan (B1/B2) |
| θF = 45 − θ |

For case 4

| |
|---|
| B1 = abs (B1) //working with magnitude |
| B2 = abs (B2) //working with magnitude |
| If B1 > B2 then |
| θ = atan (B2/B1) |
| θF = −45 − θ |
| Elseif B1 < B2 then |
| θ = atan (B1/B2) |
| θF = 0 − 135 |

At step 615 of method 600, the maximum strain is always ε=√(B1²+B2²). Since, Y is always the radius of the axle at the plane in question, the bending moment in plane 215a is calculated as follows:

$$M = \frac{\varepsilon EI}{Y} \qquad \text{Equation 22}$$

At step 620 the strain resulting from bending in plane 215b equals the half bridge output because there no axial strain to subtract, as mentioned above.

Step 625, using the bridge outputs from plane 215b, ε=√(B1²+B2²). Since Y is the radius of the axle at the plane in question, the bending moment in plane 2 can be calculated as follows:

$$M = \frac{\varepsilon EI}{Y} \qquad \text{Equation 23}$$

Steps 627-635 are performed in the same manner as outlined for the previous embodiments. In other words, now that the bending moment in each plane is known using the analytic solution applied to each plane, and now that the angle of the applied force is known, the magnitude of the applied force can be calculated in a manner equivalent to the specific embodiment given in FIG. 7. Once more, $M_1$ and $M_2$ have been calculated for strain gauge planes 215a and 215b respectively and as distances $d_2$, a and b are known, the bending moments in the respective strain gauge containing plane 215a and plane 215b is calculated as:

$$M_1 = F_1(a) + F_2(b)$$

$$M_2 = F_1(a-d_2) + F_2(b-d_2) \qquad \text{Equation 24}$$

Once more these two equations can be solved simultaneously to determine $F_1$ and $F_2$. The total resultant force in the XY plane applied by the cyclist is therefore:

$$F_{total} = F_1 + F_2 \qquad \text{Equation 25}$$

Mitigating Errors

In a two element varying half bridge linearity error due to second order terms being neglected is zero unlike the quarter bridge configuration.

The main limitation when compared to the quarter bridge configuration is the loss of out of plane (axial) force measurement. However this does not compromise the accuracy of torque/power measurement.

Specifically, due to bending in a single plane the two gauges 190 diametrically opposed undergo a resistance change equal in magnitude but opposite in sign (i.e. one in tension the other in compression). Any discrepancy in magnitude would be due to the axial strain (i.e. force in the z direction) that would result in a load on both gauges 190 which is equal in magnitude and equal in sign. Furthermore, any 'apparent strain' due to ambient temperature changes effecting the resistance of the gauges 190, would result in a load which is equal in magnitude and equal in sign (i.e. the gauges 190 are in the same ambient environment). If the two diametrically opposed gauges 190 are configured in the Wheatstone bridge configuration where two element vary, then any resistance change in the two gauges 190 which is equal in magnitude and equal in sign does not vary the output voltage from the bridge. Therefore while the force/strain in the z direction cannot be measured, temperature compensation is achieved.

Alternatives for temperature compensation in the quarter bridge configuration include using a dummy gauge 190 (i.e. the dummy gauge 190 experiences the same ambient temp effects but is subject to no strain) or measuring the ambient temperature and calculating the effect on the gauge resistance based on manufacturers calibration curves and/or experimental data.

The foregoing describes only some embodiments of the present invention, and modifications and/or changes can be made thereto without departing from the scope and spirit of the invention, the embodiments being illustrative and not restrictive.

Specifically, any number of strain gauges 190 or planes 215 may be used depending on the desired accuracy of the calculated data. For example, the force in the lateral z-axis direction may be neglected, albeit resulting in reduced accuracy in the other planes. Such an arrangement would consequentially not require diametrically opposing strain gauges.

Furthermore, the calculation of the instantaneous proportion of load shared at multiple bearing connection points attaching the pedal body and axle 210 may be simplified by assuming that the load sharing proportions are constant between the calibration and usage of the system, therefore requiring strain gauges 190 in only one plane.

APPENDIX A

Program Code
The following is an example of a function written in VBA that forms a part of the application program 133 that takes as input the six measured strains from gauges G1 to G6 as shown in the embodiment described in FIG. 5 and the angle between the axle 0° reference and the crank arm 0° reference (ThetaInit). The function also comprises code for determining the gauge highest above the neutral plane.

```
Function TCalc(G1, G2, G3, G4, G5, G6, ThetaInit)
'This is a function to calculate the instantaneous force vector
and torque for a sample of gauge data
'Thetainit is the angle measured from crank 0 degrees to axle 0
degrees +ve CCW passed in degrees, must be +ve up
'to 270, otherwise –ve complement
Pi = 3.14159265358979
'Plane 1
'First it is necessary to determine the lateral strain of G1 and
G4
strain_z14 = Abs(((Abs(G1) – Abs(G4))) / 2)
'Then determine direction of lateral force
If G1 > G4 Then
If Abs(G1) > Abs(G4) Then
strain_z14 = strain_z14 'tensile axial strain
Else
strain_z14 = –strain_z14 'compressive axial strain
End If
Else ' G1 < G4
If Abs(G1) > Abs(G4) Then
strain_z14 = –strain_z14 'compressive axial strain
Else
strain_z14 = strain_z14 'tensile axial strain
End If
End If
'therefore the bending strain in gauges 1 and 4 would be
G1 = G1 – strain_z14
G4 = G4 – strain_z14
'First it is necessary to determine the lateral strain of G2 and
strain_z23 = Abs(((Abs(G2) – Abs(G3))) / 2)
'Then determine direction of lateral force
If G2 > G3 Then
If Abs(G2) > Abs(G3) Then
strain_z23 = strain_z23 'tensile axial strain
Else
strain_z23 = –strain_z23 'compressive axial strain
End If
Else ' G2 < G3
If Abs(G2) > Abs(G3) Then
strain_z23 = –strain_z23 'compressive axial strain
Else
strain_z23 = strain_z23 'tensile axial strain
End If
End If
'therefore the bending strain in gauges 2 and 3 would be
G2 = G2 – strain_z23
```

APPENDIX A-continued

Program Code
The following is an example of a function written in VBA that forms a part of the application program 133 that takes as input the six measured strains from gauges G1 to G6 as shown in the embodiment described in FIG. 5 and the angle between the axle 0° reference and the crank arm 0° reference (ThetaInit). The function also comprises code for determining the gauge highest above the neutral plane.

```
G3 = G3 – strain_z23
'the average lateral strain is therefore
strain_z = (strain_z14 + strain_z23) / 2
'to calculate the angle of the neutral axis ThetaN measured +ve
CCW from axle 0 degree reference
'Thetaref is the acute angle from the neutral axis to a radial
line connecting the gauge whose value is the numerator
If G1 > G4 Then
If G2 > G3 Then ' –60 < ThetaN < 60
If G1 > G2 Then '0 < ThetaN < 60
thetaref = –23.545 * (G2 / G1) ^ 3 + 35.202 * (G2 / G1) ^ 2 +
48.299 * (G2 / G1)
ThetaN = 60 – thetaref
Gi = G1 'higher gauge value is more accurate for use in
moment/force calculatons
Thetai = 120 – thetaref 'to calculate the height of Gi above the
neutral axis
If Thetai > 90 Then Thetai = 180 – Thetai
Gi2# = 5 'for the force/moment calc in the second plane
Thetai2 = thetaref
Else 'G1 < G2 and –60 < ThetaN < 0
thetaref = –23.545 * (G1 / G2) ^ 3 + 35.202 * (G1 / G2) ^ 2 +
48.299 * (G1 / G2)
ThetaN = –(60 – thetaref)
Gi = G2 'higher gauge value is more accurate for use in
moment/force calculatons
Thetai = 120 – thetaref 'to calculate the height of Gi above the
neutral axis
If Thetai > 90 Then Thetai = 180 – Thetai
Gi2# = 5 'for the force/moment calc in the second plane
Thetai2 = Thetai
End If
Else 'G2 < G3 and 60 < ThetaN < 120
If G1 > G3 Then '60 < ThetaN < 90
thetaref = 6.5551 * (G3 / G1) ^ 3 – 26.256 * (G3 / G1) ^ 2 +
49.713 * (G3 / G1)
ThetaN = 60 + thetaref
Gi = G1 'higher gauge value is more accurate for use in
moment/force calculatons
Thetai = 60 – thetaref 'to calculate the height of Gi above the
neutral axis
Gi2# = 6 'for the force/moment calc in the second plane
Thetai2 = thetaref
Else 'G1 < G3 and 90 < ThetaN < 120
thetaref = 6.5551 * (G1 / G3) ^ 3 – 26.256 * (G1 / G3) ^ 2 +
49.713 * (G1 / G3)
ThetaN = 120 – thetaref
Gi = G3 'higher gauge value is more accurate for use in
moment/force calculatons
Thetai = 60 – thetaref 'to calculate the height of Gi above the
neutral axis
Gi2# = 6 'for the force/moment calc in the second plane
Thetai2 = Thetai
End If
End If
Else 'G1 < G4
If G2 > G3 Then '–120 < ThetaN < –60
If G2 > G4 Then ' –90 < ThetaN < –60
thetaref = 6.5551 * (G4 / G2) ^ 3 – 26.256 * (G4 / G2) ^ 2 +
49.713 * (G4 / G2)
ThetaN = –60 – thetaref
Gi = G2 'higher gauge value is more accurate for use in
moment/force calculatons
Thetai = 60 – thetaref 'to calculate the height of Gi above the
neutral axis
Gi2# = 5 'for the force/moment calc in the second plane
Thetai2 = Thetai
Else ' G2 < G4 and –120 < ThetaN < –90
thetaref = 6.5551 * (G2 / G4) ^ 3 – 26.256 * (G2 / G4) ^ 2 +
49.713 * (G2 / G4)
ThetaN = –(120 – thetaref)
Gi = G4 'higher gauge value is more accurate for use in
```

APPENDIX A-continued

Program Code
The following is an example of a function written in VBA that forms a part of the application program 133 that takes as input the six measured strains from gauges G1 to G6 as shown in the embodiment described in FIG. 5 and the angle between the axle 0° reference and the crank arm 0° reference (ThetaInit). The function also comprises code for determining the gauge highest above the neutral plane.

```
moment/force calculatons
        Thetai = 60 - thetaref 'to calculate the height of Gi above the
neutral axis
        Gi2# = 5 'for the force/moment calc in the second plane
        Thetai2 = thetaref
        End If
        Else 'G2 < G3 and 120 < ThetaN < 240
        If G3 > G4 Then '120 < ThetaN < 180
        thetaref = -23.545 * (G4 / G3) ^ 3 + 35.202 * (G4 / G3) ^ 2 +
48.299 * (G4 / G3)
        ThetaN = 120 + thetaref
        Gi = G3 'higher gauge value is more accurate for use in
moment/force calculatons
        Thetai = 120 - thetaref 'to calculate the height of Gi above the
neutral axis
           If Thetai > 90 Then Thetai = 180 - Thetai
           Gi2# = 6 'for the force/moment calc in the second plane
           Thetai2 = Thetai
        Else 'G3 < G4 and 180 < ThetaN < 240
        thetaref = -23.545 * (G3 / G4) ^ 3 + 35.202 * (G3 / G4) ^ 2 +
48.299 * (G3 / G4)
        ThetaN = 240 - thetaref
        Gi = G4 'higher gauge value is more accurate for use in
moment/force calculatons
        Thetai = 120 - thetaref 'to calculate the height of Gi above the
neutral axis
           If Thetai > 90 Then Thetai = 180 - Thetai
           Gi2# = '6 for the force/moment calc in the second plane
           Thetai2 = thetaref
        End If
        End If
        End If
        'To comply with a positive requirement for ThetaF
        If ThetaN < 0 Then ThetaN = 360 + ThetaN
        'ThetaN_crank is the angle of the neutral axis measured +ve CCW
from crank 0 degree reference
        ThetaN_crank = ThetaN + ThetaInit
        'ThetaF is the angle of the applied force (sum of normal and
tangential) measured +ve CCW from crank 0 degree reference
        ThetaF = ThetaN_crank + 90
        If ThetaF > 360 Then ThetaF = ThetaF - 360
        'To calculate the bending moment in plane 1 (M1)- based on
analytical parameters: I = 5.153e-9 m^4, E = 200e9 Pa. Note that gauge
data is passed in microstrain and therefore needs to be adjusted by 10 -6
        M1 = (200000000000# * 0.000000005153 * Gi * 10 ^ -6) / ((18 /
2000) * Sin(Thetai * (Pi / 180))) 'The bending moment in Nm
        'In plane 2
        'First the portion of lateral strain is calculated
        strain_z56 = Abs((Abs(G5) - Abs(G6)) / 2)
        'The direction of the lateral strain in this plane
        If G5 > G6 Then
           If Abs(G5) > Abs(G6) Then
           strain_z56 = strain_z56 'tensile axial strain
           Else ' abs(G5)<abs(G6)
           strain_z56 = -strain_z56 'compressive axial strain
           End If
        Else ' G5 < G6
           If Abs(G5) > Abs(G6) Then
           strain_z56 = -strain_z56 'tensile axial strain
           Else ' abs(G5)<abs(G6)
           strain_z56 = strain_z56 'compressive axial strain
           End If
        End If
        'Therefore the bending strain in G5 and G6 is
        G5 = G5 - strain_z56
        G6 = G6 - strain_z56
        'update
        If Gi2# = 5 Then Gi2 = G5
        If Gi2# = 6 Then Gi2 = G6
        'The bending moment in this plane is calculated from analytical
data: d=7.8mm I=1.817e-10 E=200e9
        M2 = (200000000000# * Gi2 * 10 ^ -6 * 0.0000000001817) /
((7.8 / 2000) * Sin(Thetai2 * (Pi / 180)))
        'the force at bearing 1 (F1) and bearing 2 (F2) are calculated
based on known distances in the pedal axle
        F2 = M2 / 0.00974
        F1 = (M1 - F2 * 0.04389) / 0.01095
        Ftotal = F1 + F2
        'the normal and tangential force components are therefore
        If 0 <= ThetaF <= 90 Then
           Ftan = -Ftotal * (Cos(ThetaF * (Pi / 180)))
           Fnorm = Ftotal * (Sin(ThetaF * (Pi / 180)))
        ElseIf 90 < ThetaF <= 180 Then
           Ftan = Ftotal * (Cos((180 - ThetaF) * (Pi / 180)))
           Fnorm = Ftotal * (Sin((180 - ThetaF) * (Pi / 180)))
        ElseIf 180 < ThetaF <= 270 Then
           Ftan = Ftotal * (Cos((ThetaF - 180) * (Pi / 180)))
           Fnorm = -Ftotal * (Sin((ThetaF - 180) * (Pi / 180)))
        ElseIf 270 < ThetaF <= 360 Then
           Ftan = -Ftotal * (Cos((360 - ThetaF) * (Pi / 180)))
           Fnorm = -Ftotal * (Sin((360 - ThetaF) * (Pi / 180)))
        End If
        'The torque (T) is - based on a 175mm crank length
        T = Fnorm * 0.175
        'The lateral force (Fz) is: based on area of 2.5447e-4 E=200e9
        Fz = strain_z * 0.00025447 * 200000#
        TCalc = Array(M1, M2, T, Fz, Ftan, Fnorm, Ftotal, ThetaF)
Returns the calculated values
        End Function
```

The invention claimed is:

1. A method for determining the torque applied to a pedal axle under load, the method comprising:
   measuring the strain experienced by said pedal axle as a result of said load by measuring the strain at two points on the surface of said pedal axle, said two points being coplanar to a plane and spaced apart at an angle other than 90°, said plane being substantially perpendicular to said axle;
   determining the orientation of said load from said strain measurement;
   determining the magnitude of said load using the numerical relationship between said strain and said magnitude; and
   determining torque from said orientation and said magnitude.

2. The method of claim 1, wherein said strain measuring comprises:
   measuring the strain at two points on the surface of said pedal axle, said two points being coplanar to a first plane and spaced apart at an angle other than 90°, said first plane being substantially perpendicular to said axle; and
   measuring the strain at a further two points on the surface of said pedal axle, said further two points being coplanar to a second plane and spaced apart at an angle other than 90°, said second plane being substantially perpendicular to said axle.

3. The method of claim 1, wherein said angle is at least one of 60° and 120°.

4. The method of claim 1, wherein determining said orientation comprises:
   calculating the strain resulting from the bending moment of said axle;

determining said orientation from a polynomial relationship between said strain resulting from the bending and said orientation.

5. The method of claim 1, wherein determining said magnitude of said load comprises:
   calculating the bending moment of said axle; and
   determining said magnitude of said load using the numerical relationship between said bending moment and said magnitude of said load.

6. The method of claim 1, wherein said torque is determined as the product of said magnitude of said load and the length of the crank attached to said pedal axle.

7. The method of claim 1, further comprising determining the power applied to said pedal.

8. The method of claim 7, wherein said power is determined as the product of said torque and the angular velocity of said pedal axle.

9. The method of claim 8, wherein said angular velocity is determined from the time taken for said pedal axle to complete a revolution, and said time taken for said pedal axle to complete a revolution is determined from said orientation of said load.

10. A method for determining the torque applied to a pedal axle under load, the method comprising:
    measuring the strain experienced by said pedal axle as a result of said load;
    determining the orientation of said load from said strain measurement;
    determining the magnitude of said load from said strain measurement by calculating the bending moment of said axle, and determining said magnitude of said load using the numerical relationship between said bending moment and said magnitude; and
    determining torque from said orientation and said magnitude.

11. A method for determining the orientation of a pedal axle under load, the method comprising:
    measuring the strain experienced by said pedal axle as a result of said load by measuring the strain at two points on the surface of said pedal axle, said two points being coplanar to a plane and spaced apart at an angle other than 90°, said plane being substantially perpendicular to said axle; and
    determining the orientation of said load from said strain measurement.

12. An apparatus for determining the torque applied to a pedal axle under load, the apparatus comprising:
    a strain gauge configured to measure the strain experienced by said pedal axle as a result of said load by measuring the strain at two points on the surface of said pedal axle, said two points being coplanar to a plane and spaced apart at an angle other than 90°, said plane being substantially perpendicular to said axle; and
    a processor configured to determine the orientation of said load from said strain measurement, to determine the magnitude of said load using the numerical relationship between said strain and said magnitude, and to determine said torque from said orientation and said magnitude.

13. The apparatus of claim 12, wherein said strain gauge comprises:
    two strain gauges configured to measure the strain at two points on the surface of said pedal axle, said two points being coplanar to a first plane and spaced apart at an angle other than 90°, said first plane being substantially perpendicular to said axle; and
    two strain gauges configured to measure the strain at a further two points on the surface of said pedal axle, said further two points being coplanar to a second plane and spaced apart at an angle other than 90°, said second plane being substantially perpendicular to said axle.

14. The apparatus of claim 12, wherein said angle is at least one of 60° and 120°.

15. The apparatus of claim 12, wherein said processor is configured to determine said orientation by calculating the strain resulting from the bending moment of said axle and determining said orientation from a polynomial relationship between said strain resulting from the bending and said orientation.

16. The apparatus of claim 12, wherein said processor is configured to determine said magnitude of said load by calculating the bending moment of said axle and configured to determine said magnitude of said load using the numerical relationship between said bending moment and said magnitude of said load.

17. The apparatus of claim 12, wherein said processor is configured to determine said torque as the product of said magnitude of said load and the length of the crank attached to said pedal axle.

18. The apparatus of claim 12, wherein said processor is configured to determine the power applied to said pedal.

19. The apparatus of claim 18, wherein said processor is configured to determine said power as the product of said torque and the angular velocity of said pedal axle.

20. The apparatus of claim 19, wherein said processor is configured to determine said velocity from the time taken for said pedal axle to complete a revolution, and to determine said time taken for said pedal axle to complete a revolution from said orientation of said load.

21. An apparatus for determining the torque applied to a pedal axle under load, the apparatus comprising:
    a strain gauge configured to measure the strain experienced by said pedal axle as a result of said load; and
    a processor configured to determine the orientation of said load from said load measurement, to determine the magnitude of said load from said strain measurement by calculating the bending moment of said axle and determining said magnitude of said load using the numerical relationship between said bending moment and said magnitude, and to determine said torque from said orientation and said magnitude.

22. An apparatus for determining the orientation of a pedal axle under load, the apparatus comprising:
    a strain gauge configured to measure the strain experienced by said pedal axle as a result of said load by measuring the strain at two points on the surface of said pedal axle, said two points being coplanar to a plane and spaced apart at an angle other than 90°, said plane being substantially perpendicular to said axle; and
    a processor configured determining the orientation of said load from said strain measurement, to determine the magnitude of said load from said strain measurement, and to determine said torque from said orientation and said magnitude.

23. A computer readable storage medium having a computer program recorded therein, the program being executable by a computer apparatus to make the computer determine the torque applied to a pedal axle under load, said program comprising:
    code for measuring the strain experienced by said pedal axle as a result of said load by measuring the strain at two points on the surface of said pedal axle, said two points being coplanar to a plane and spaced apart at an angle other than 90°, said plane being substantially perpendicular to said axle;

code for determining the orientation of said load from said strain measurement;

code for determining the magnitude of said load using the numerical relationship between said strain and said magnitude; and code for determining said torque from said orientation and said magnitude.

24. The medium claim of 23, wherein said program comprises code for measuring the strain at two points on the surface of said pedal axle, said two points being coplanar to a first plane and spaced apart at an angle other than 90°, said first plane being substantially perpendicular to said axle; and code for measuring the strain at a further two points on the surface of said pedal axle, said further two points being coplanar to a second plane and spaced apart at an angle other than 90°, said second plane being substantially perpendicular to said axle.

25. The medium of claim 23, wherein said angle is at least one of 60° and 120°.

26. The medium of claim 23, wherein said program comprises code for calculating the strain resulting from the bending moment of said axle; and code for determining said orientation from a polynomial relationship between said strain resulting from the bending and said orientation.

27. The medium of claim 23, wherein said program comprises code for calculating the bending moment of said axle and code for determining said magnitude of said load using the numerical relationship between said bending moment and said magnitude of said load.

28. The medium of claim 23, wherein said program comprises code for determining said torque as the product of said magnitude of said load and the length of the crank attached to said pedal axle.

29. The medium of claim 23, wherein said program comprises code for determining the power applied to said pedal.

30. The medium of claim 29, wherein said program comprises code for determining said power as the product of said torque and the velocity of said pedal axle.

31. The medium of claim 30, wherein said program comprises code for determining said velocity from the time taken for said pedal axle to complete a revolution and code for determining said time taken for said pedal axle to complete a revolution from said orientation of said load.

32. A computer readable storage medium having a computer program recorded therein, the program being executable by a computer apparatus to make the computer determine the torque applied to a pedal axle under load, said program comprising:

code for measuring the strain experienced by said pedal axle as a result of said load;

code for determining the orientation of said load from said strain measurement;

code for determining the magnitude of said load from said strain measurement by calculating the bending moment of said axle, and determining said magnitude of said load using the numerical relationship between said bending moment and said magnitude; and code for determining torque from said orientation and said magnitude.

33. A computer readable storage medium having a computer program recorded therein, the program being executable by a computer apparatus to make the computer determine the orientation of a pedal axle under load, said program comprising:

code for measuring the strain experienced by said pedal axle as a result of said load by measuring the strain at two points on the surface of said pedal axle, said two points being coplanar to a plane and spaced apart at an angle other than 90°, said plane being substantially perpendicular to said axle; and code for determining the orientation of said load from said strain measurement.

* * * * *